United States Patent
Pflaster et al.

(10) Patent No.: US 10,314,680 B2
(45) Date of Patent: *Jun. 11, 2019

(54) LIMB PROTECTION DEVICE

(71) Applicant: Horsepower Technologies Inc., Lowell, MA (US)

(72) Inventors: Daniel Scott Pflaster, Charlotte, VT (US); Joseph J. Crisco, Barrington, RI (US); Carl A. Kirker-Head, Sturbridge, MA (US); Russell D. Fiore, Lincoln, RI (US); Wendy Drumm, Providence, RI (US); Richard L. Miller, Needham, MA (US); Kristin Jugenheimer Size, Waltham, MA (US); Gregory Scott Torrisi, Midlothian, VA (US); Peter Swai, Wakefield, MA (US); Jennifer Linnane, Melrose, MA (US); Christopher John Morse, Malden, MA (US)

(73) Assignee: Horsepower Technologies Inc., Lowell, MA (US)

(*) Notice: Subject to any disclaimer, the term of this patent is extended or adjusted under 35 U.S.C. 154(b) by 392 days.

This patent is subject to a terminal disclaimer.

(21) Appl. No.: 14/999,810

(22) Filed: Jul. 1, 2016

(65) Prior Publication Data

US 2016/0346070 A1 Dec. 1, 2016

Related U.S. Application Data

(63) Continuation-in-part of application No. 14/106,300, filed on Dec. 13, 2013, now Pat. No. 9,427,347,
(Continued)

(51) Int. Cl.
*A61B 5/11* (2006.01)
*A61D 9/00* (2006.01)
(Continued)

(52) U.S. Cl.
CPC .............. *A61D 9/00* (2013.01); *A01K 13/007* (2013.01); *A61B 5/1071* (2013.01);
(Continued)

(58) Field of Classification Search
CPC ...... A61F 2005/0139; A61F 2005/0165; A61F 2005/0167; A61F 5/0102; A61F 5/0111;
(Continued)

(56) References Cited

U.S. PATENT DOCUMENTS

| 121,880 A | 12/1871 | Lewis |
| 901,582 A | 10/1908 | Clegg |

(Continued)

FOREIGN PATENT DOCUMENTS

EP 1 449 497 A2 8/2004

*Primary Examiner* — Kari K Rodriquez
(74) *Attorney, Agent, or Firm* — Foley & Lardner LLP

(57) ABSTRACT

A joint-supporting device comprises tensile members extending from a proximal cuff secured to the limb above the joint to a distal cuff secured to the limb below the joint, supplementing the tensile characteristics of the joint's tendons, ligaments, and other structure. The device may also comprise structure for limiting the range of motion and angular velocity of the joint.

5 Claims, 17 Drawing Sheets

Related U.S. Application Data which is a continuation-in-part of application No. 13/694,621, filed on Dec. 18, 2012, now Pat. No. 9,044,306, which is a continuation-in-part of application No. 13/064,644, filed on Apr. 5, 2011, now Pat. No. 8,894,594.

(60) Provisional application No. 61/321,212, filed on Apr. 6, 2010.

(51) Int. Cl.
    *A61F 5/01*     (2006.01)
    *A01K 13/00*     (2006.01)
    *A61B 5/107*     (2006.01)
    *A61D 99/00*     (2006.01)

(52) U.S. Cl.
    CPC ............ *A61B 5/1121* (2013.01); *A61D 99/00* (2013.01); *A61F 5/0102* (2013.01); *A61F 5/0111* (2013.01); *A61B 2503/40* (2013.01); *A61F 2005/0167* (2013.01); *A61F 2005/0172* (2013.01); *A61F 2005/0179* (2013.01)

(58) Field of Classification Search
    CPC ... A61F 5/0127; A61F 2005/0172–2005/0179; A61K 13/006; A61K 13/007; A61D 9/00; A61D 9/02; A61D 99/00
    USPC ............... 119/816, 817, 820, 850, 856, 863; 602/12, 16, 20–29; 54/82
    See application file for complete search history.

(56) References Cited

U.S. PATENT DOCUMENTS

| | | |
|---|---|---|
| 2,512,925 A | 6/1950 | Eggeman |
| 2,937,487 A | 5/1960 | Dever |
| 3,193,984 A | 7/1965 | Schubert |
| 3,209,517 A | 10/1965 | Hyman |
| 3,439,670 A | 4/1969 | Schuerch |
| 4,099,269 A | 7/1978 | Porner |
| 4,370,977 A | 2/1983 | Mauldin et al. |
| 4,471,538 A | 9/1984 | Pomeranz |
| 4,538,602 A | 9/1985 | Shapiro |
| 4,961,416 A | 10/1990 | Moore |
| 5,107,827 A | 4/1992 | Boyd |
| 5,115,627 A | 5/1992 | Scott |
| 5,152,285 A | 10/1992 | Gnegy |
| 5,201,776 A | 4/1993 | Freeman |
| 5,363,632 A | 11/1994 | Amato |
| 5,376,066 A | 12/1994 | Phillips et al. |
| 5,441,015 A | 8/1995 | Farley |
| 5,545,128 A | 8/1996 | Hayes et al. |
| 5,579,627 A | 12/1996 | Vogt |
| 5,599,290 A | 2/1997 | Hayes et al. |
| 5,658,241 A | 8/1997 | Deharde |
| 5,672,152 A | 9/1997 | Mason |
| 5,794,261 A | 8/1998 | Hefling |
| 5,816,032 A | 10/1998 | Vogt |
| 5,827,208 A | 10/1998 | Mason |
| 5,861,175 A | 1/1999 | Walters et al. |
| 5,871,458 A | 2/1999 | Detty |
| 5,910,126 A | 6/1999 | Wilson et al. |
| 6,033,373 A | 3/2000 | Davis |
| 6,039,709 A | 3/2000 | Bzoch |
| 6,117,097 A | 9/2000 | Ruiz |
| 6,151,873 A | 11/2000 | Rogers |
| 6,368,613 B1 | 4/2002 | Walters et al. |
| 6,387,066 B1 | 5/2002 | Whiteside |
| 6,553,994 B2 | 4/2003 | Bard |
| 6,883,466 B1 | 4/2005 | Chambers |
| 6,918,236 B2 | 7/2005 | Springs |
| 7,402,147 B1 | 7/2008 | Allen |
| 7,559,910 B2 | 6/2009 | Daly |
| 7,789,844 B1 | 9/2010 | Allen |
| 7,837,640 B2 | 11/2010 | Greenwald et al. |
| 7,896,019 B2 | 3/2011 | Bettin et al. |
| 2002/0077368 A1 | 6/2002 | Walters et al. |
| 2003/0153853 A1 | 8/2003 | Houser |
| 2004/0055543 A1 | 5/2004 | Clement |
| 2004/0255955 A1 | 12/2004 | Daly |
| 2005/0059908 A1 | 3/2005 | Bogert |
| 2005/0187505 A1 | 8/2005 | Carlson |
| 2006/0107909 A1 | 5/2006 | White |
| 2006/0155230 A1 | 7/2006 | Mason |
| 2006/0231045 A1 | 10/2006 | Lindley |
| 2008/0200856 A1 | 8/2008 | Cadichon |
| 2009/0094949 A1 | 4/2009 | Heid et al. |
| 2009/0137935 A1 | 5/2009 | Nace |
| 2009/0288377 A1 | 11/2009 | Heid et al. |
| 2010/0056973 A1 | 3/2010 | Farrow et al. |
| 2010/0100021 A1 | 4/2010 | Einarsson |
| 2010/0132099 A1 | 6/2010 | Green et al. |
| 2010/0192290 A1 | 8/2010 | Husain |
| 2011/0034848 A1 | 2/2011 | Lutz |
| 2014/0148746 A1 | 5/2014 | Pflaster |

For 2 springs in parallel:

$k_{effective} = k_{fetlock} + k_{device}$ ;

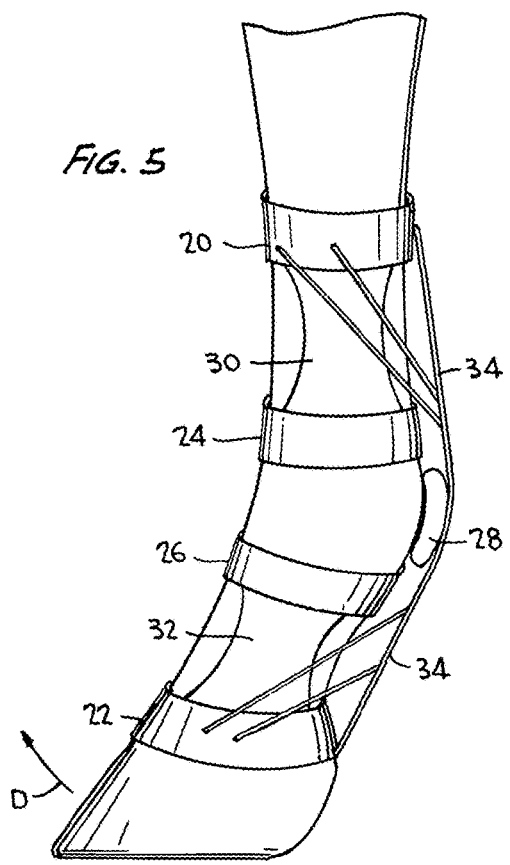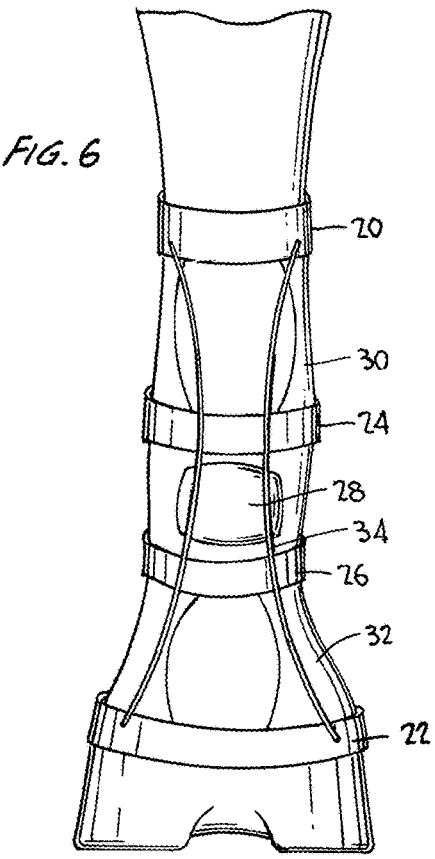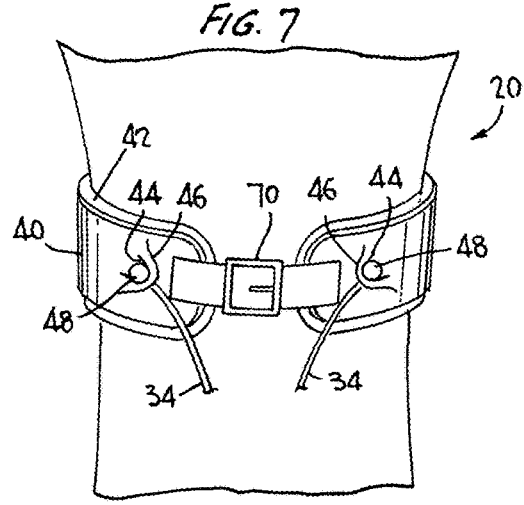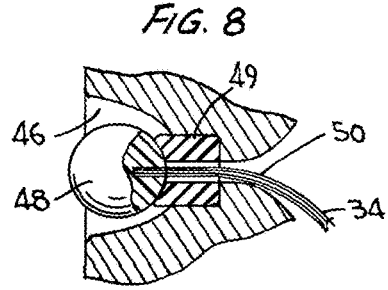

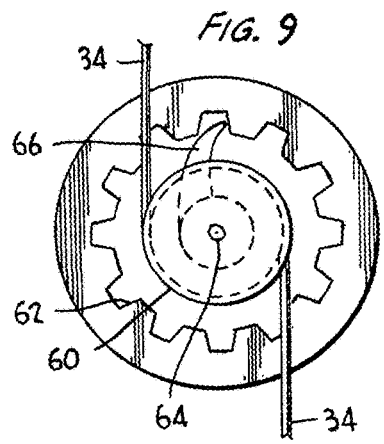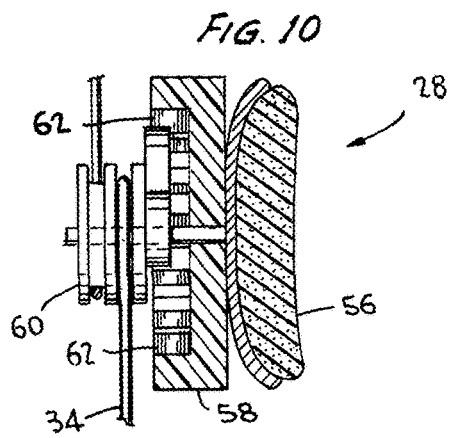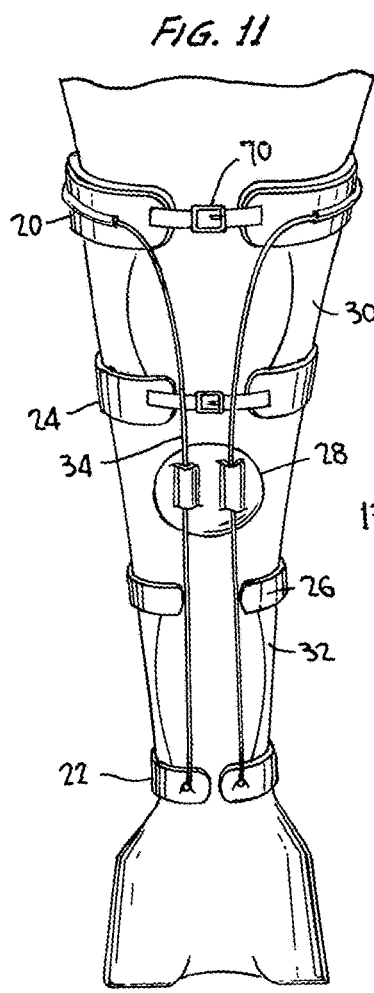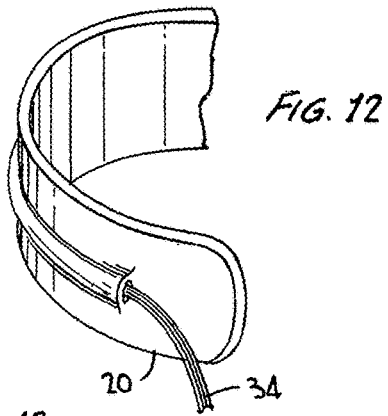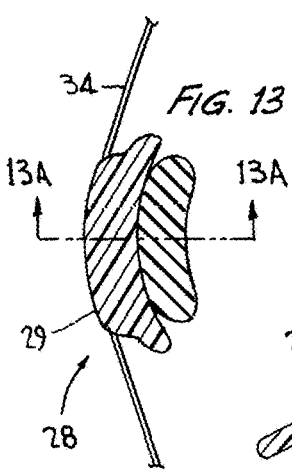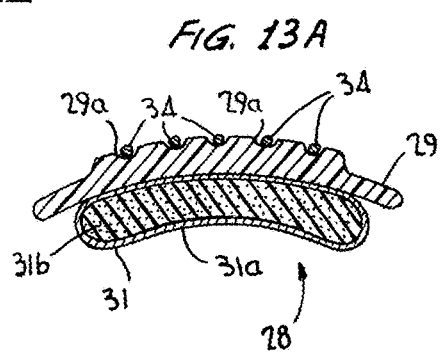

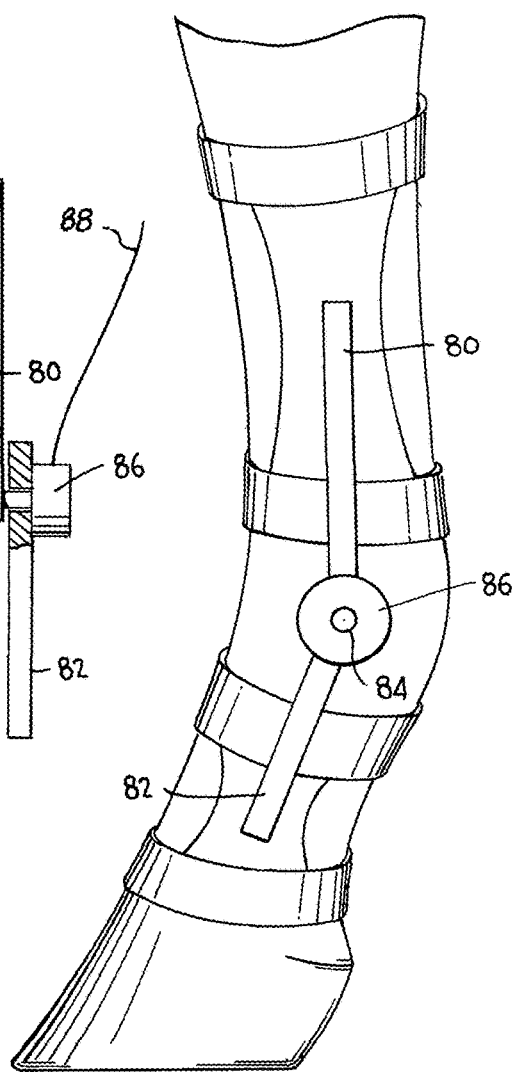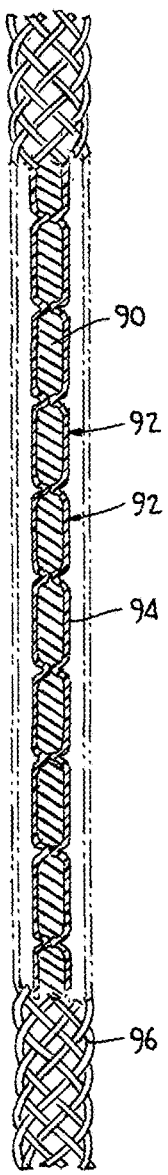

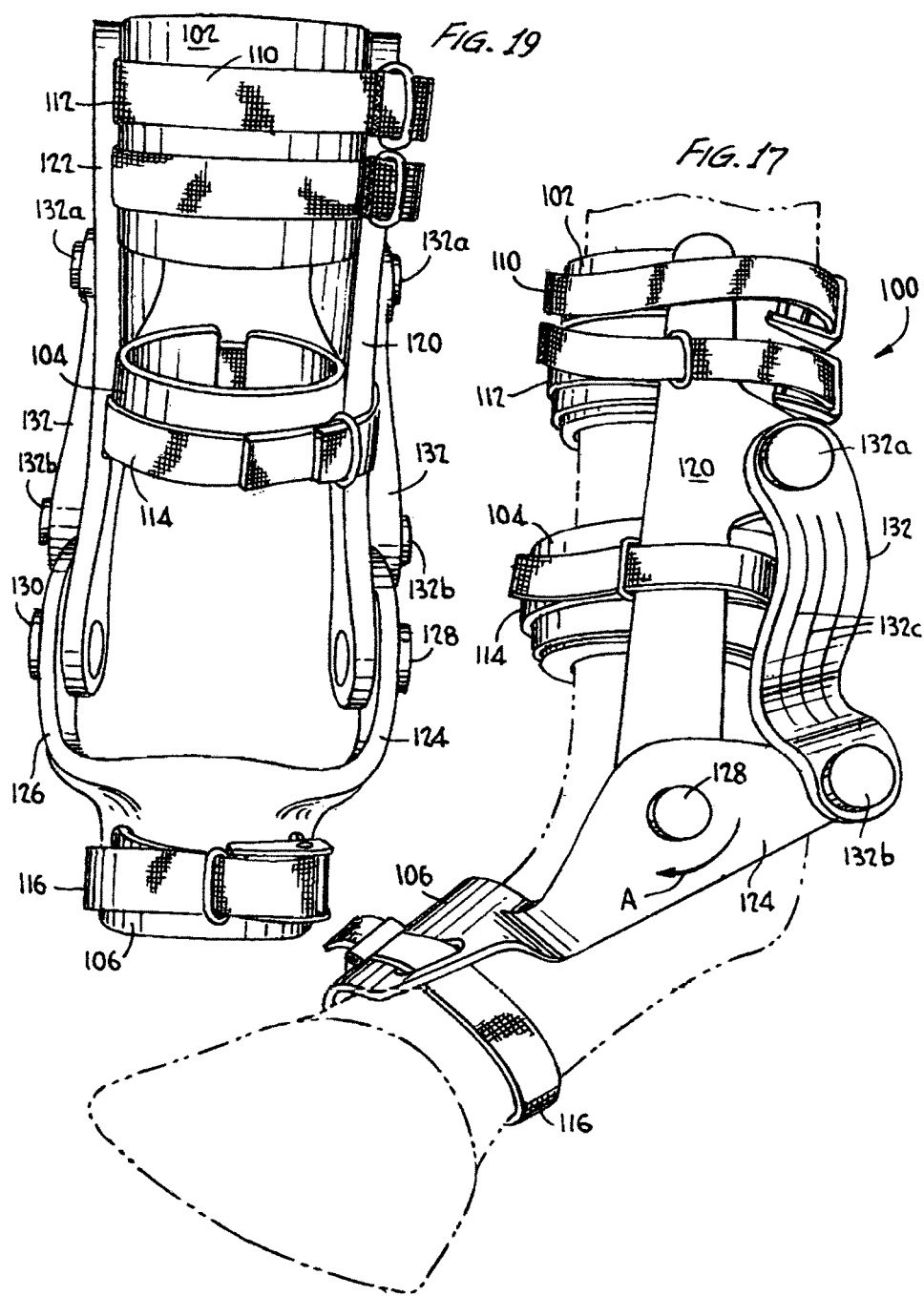

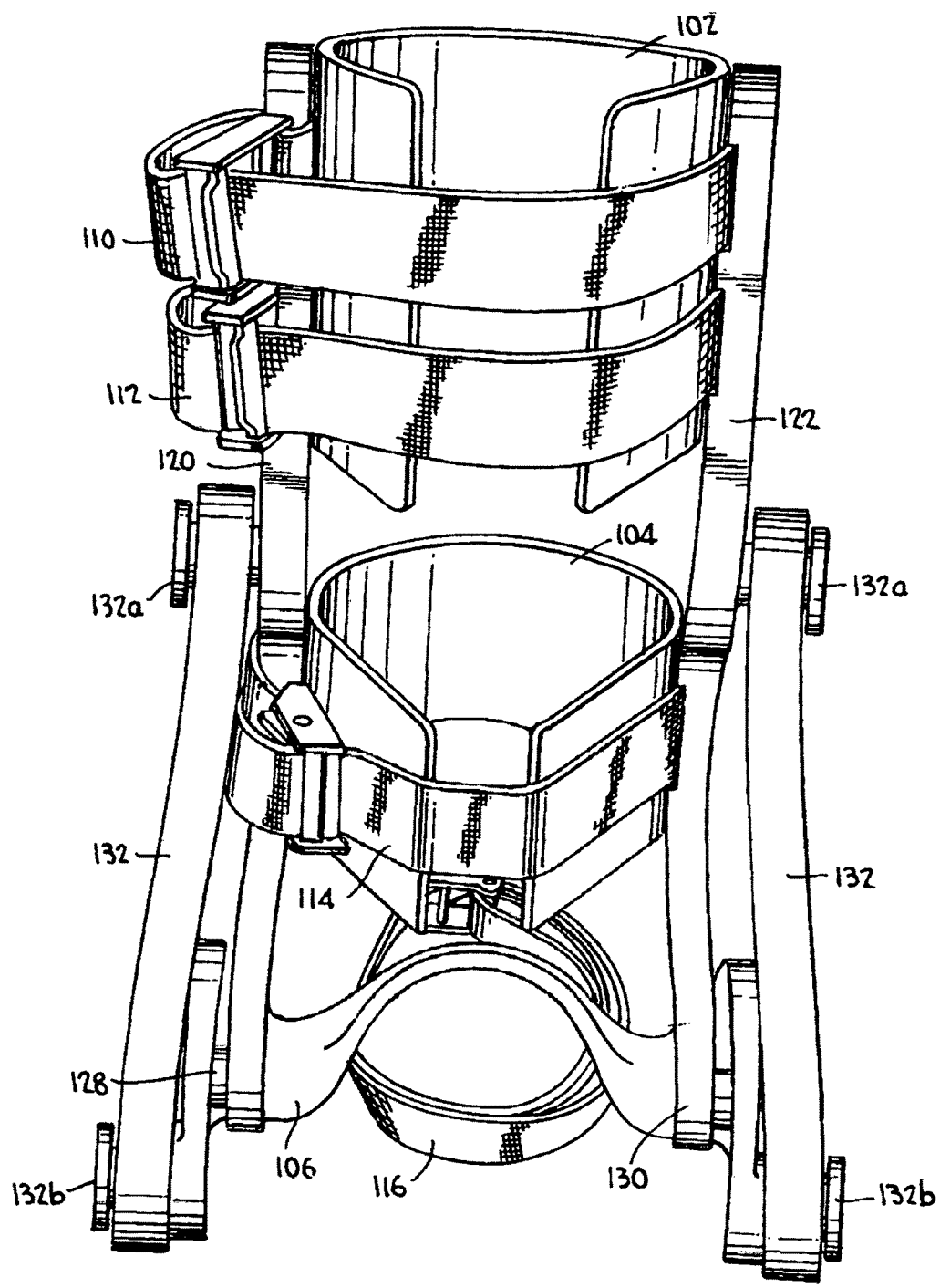

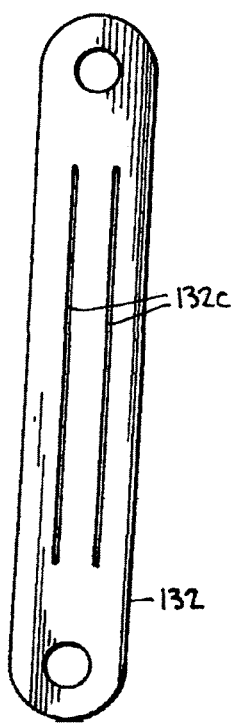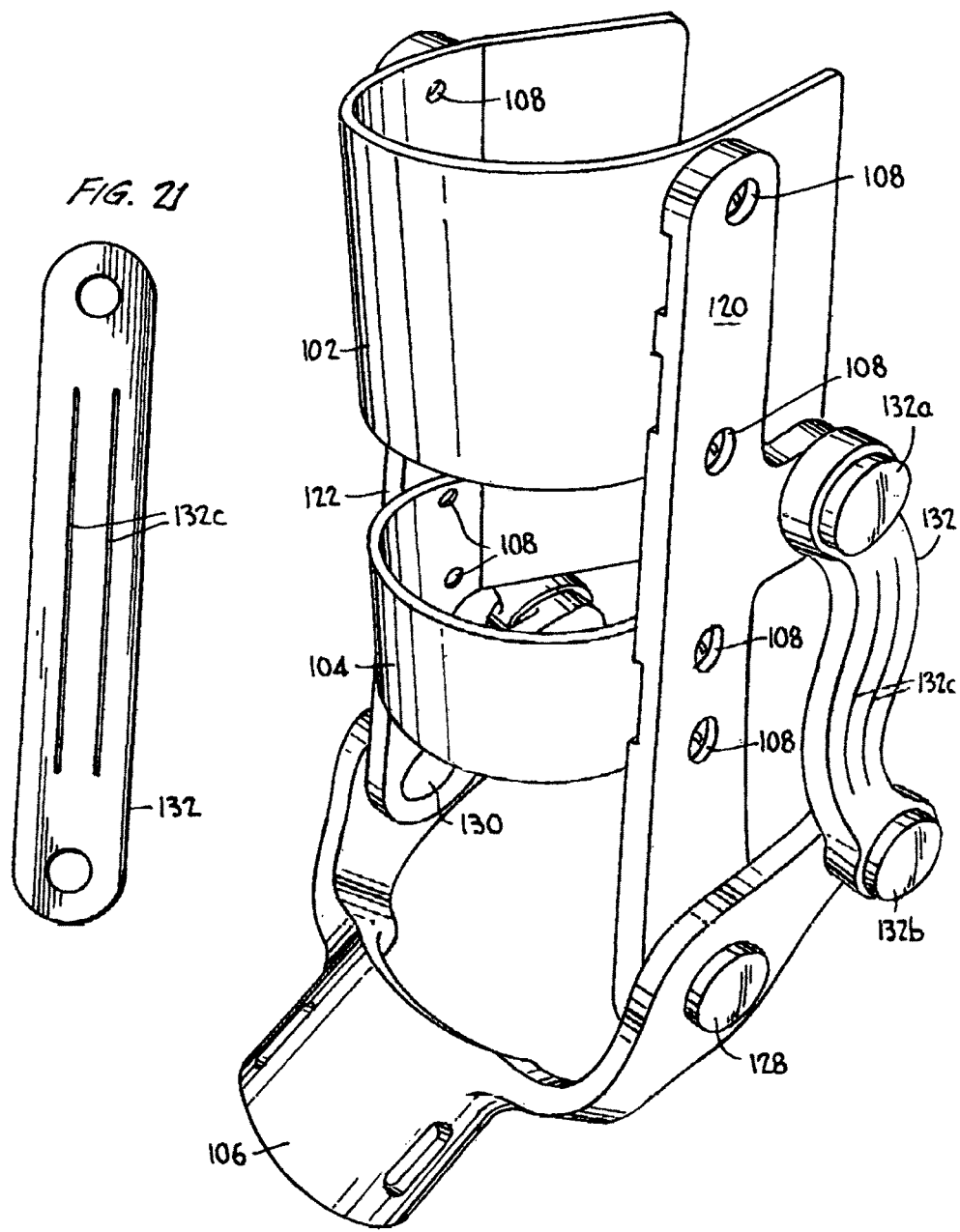

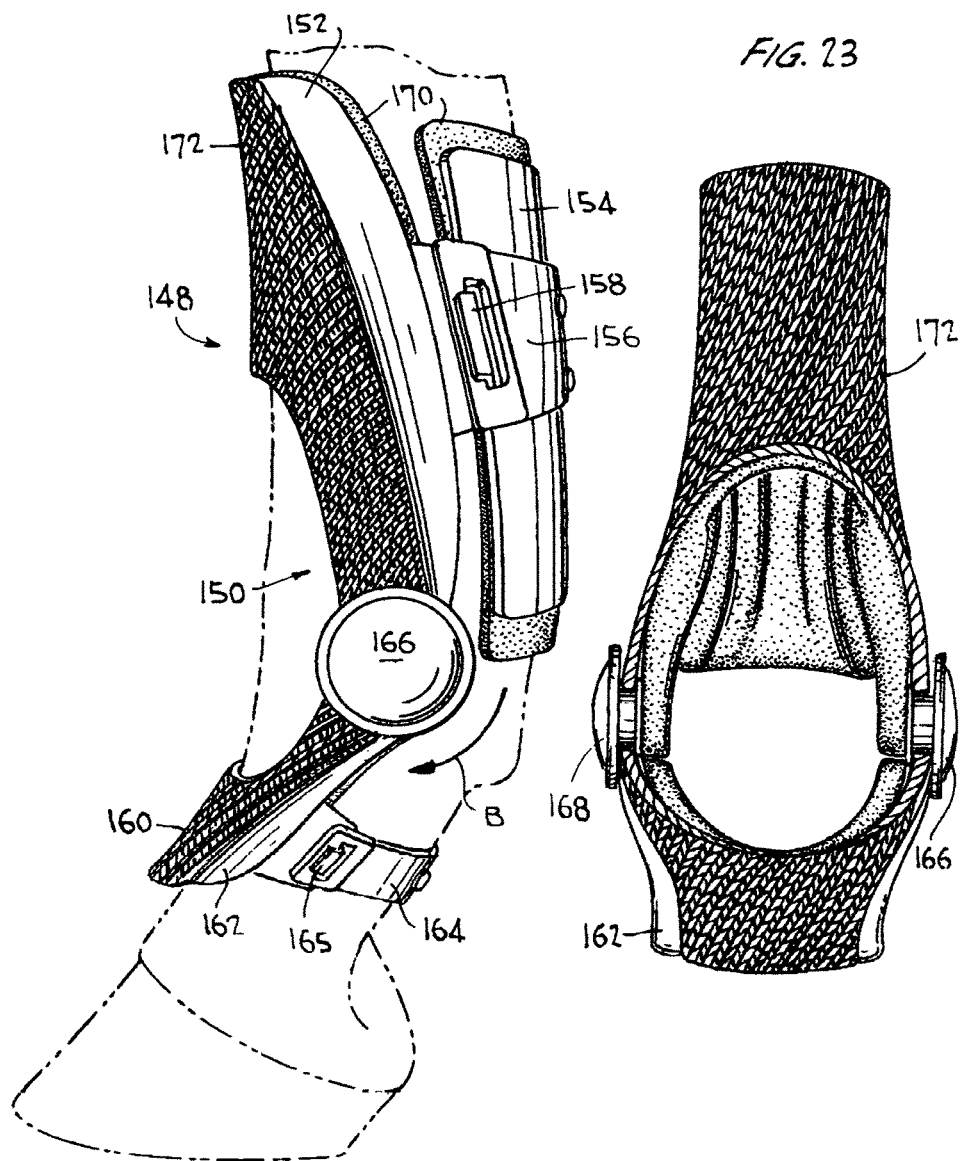

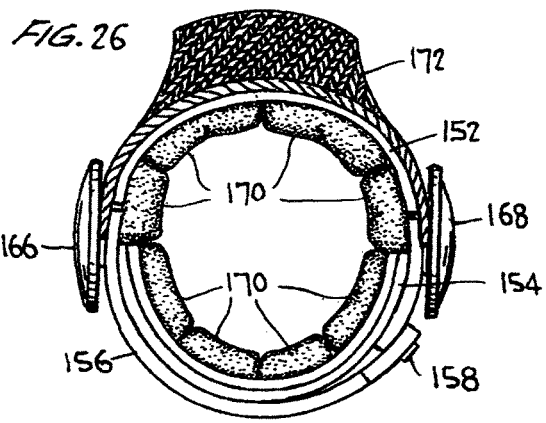
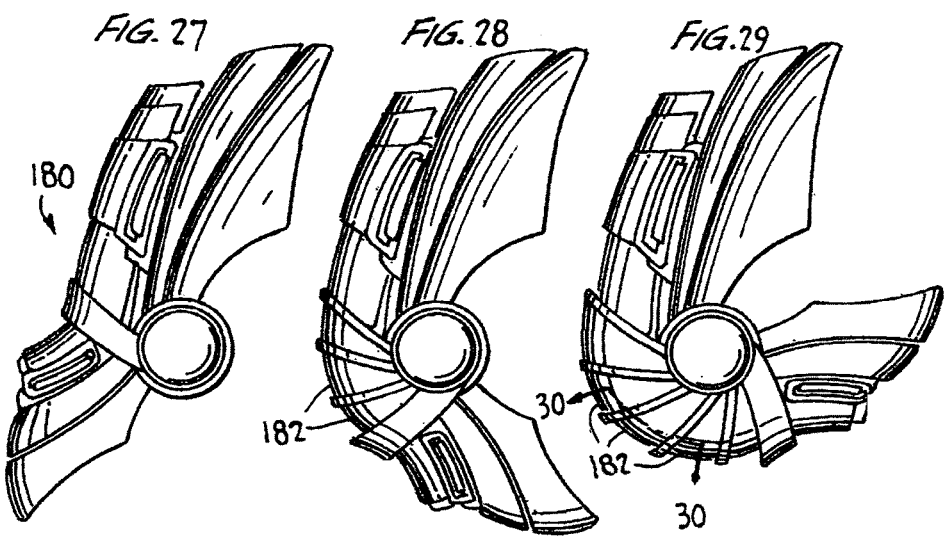
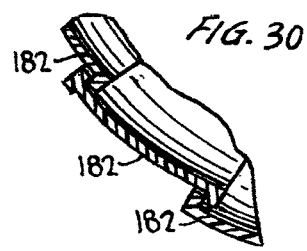

SECTION B-B

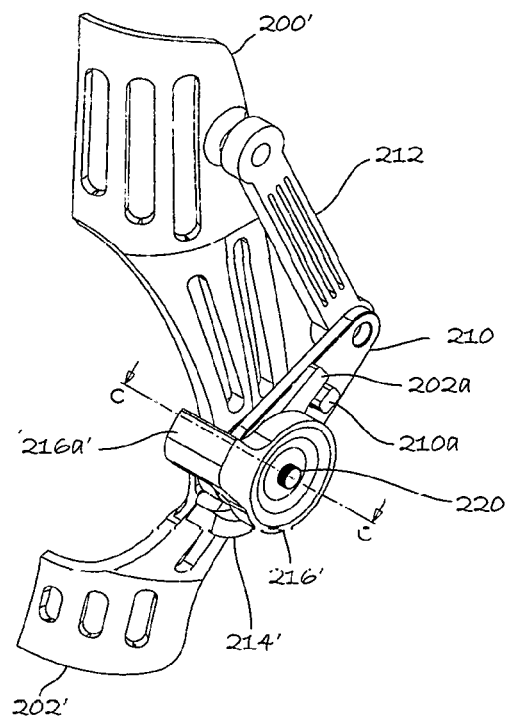
Fig. 39
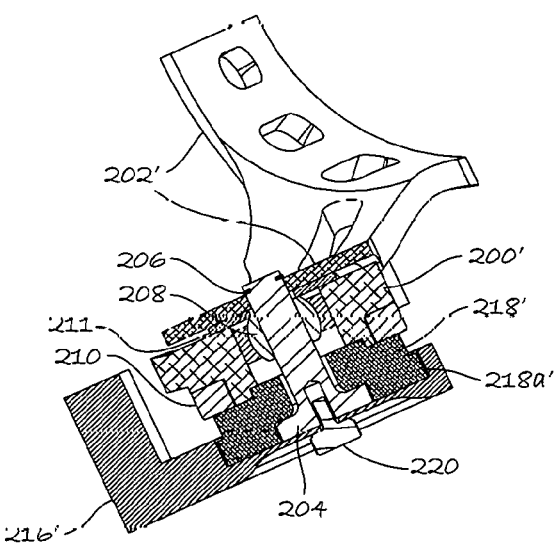
Fig. 40 - Section C-C

LIMB PROTECTION DEVICE

CROSS-REFERENCE TO RELATED APPLICATION

This application is a continuation-in-part of Ser. No. 14/106,300, filed Dec. 13, 2013, which was a continuation-in-part of Ser. No. 13/694,621, filed Dec. 18, 2012, now U.S. Pat. No. 9,044,306, which was a continuation-in-part of Ser. No. 13/064,644, filed Apr. 5, 2011, now U.S. Pat. No. 8,894,594, which claims priority from Provisional Patent Application Ser. No. 61/321,212, filed Apr. 6, 2010.

FIELD OF THE INVENTION

The invention herein relates to a device to prevent damage to body joints, in particular to prevent injury to both hard and soft tissues, e.g., during athletic activity, and also for support during rehabilitation from injury or surgery. The invention is described in several embodiments optimized for prevention of equine lower limb injuries and for rehabilitation thereof, but is not limited thereto.

More specifically, the invention is disclosed in a first embodiment, represented by FIGS. 5-13A and 16, in which the joint protective device comprises proximal and distal structures secured to the limb on either side of the joint to be protected. Tensile members which are not resilient extend from the proximal structure to the distal structure to support the joint and limit its range of motion. Dilatant materials may be provided to limit the angular velocity of the joint. The proximal and distal structures are not joined to one another, such that in order that the tensile members can effectively support the joint, the proximal and distal structures must be secured to the limb in a manner that prevents relative motion.

In the remaining embodiments, the proximal and distal structures are joined to one another so as to allow relative rotation about an axis substantially coaxial with the axis of rotation of the joint to be protected.

In a second embodiment, represented by FIGS. 17-21, resilient tensile members extend between the proximal and distal structures so as to store energy when the joint is extended, thereby helping support the joint.

In a third embodiment, represented by FIGS. 22-26, springs are provided between the proximal and distal structures so as to store energy when the joint is extended, thereby helping support the joint.

In a fourth embodiment, represented by FIGS. 31-36, resilient tensile members again extend between the proximal and distal structures so as to store energy when the joint is extended, thereby helping support the joint. This embodiment differs from that of FIGS. 17-21 in that a linkage is provided so as to disengage the resilient tensile members when the joint goes into flexion, and in other ways. According to a further refinement shown in FIGS. 33-36, an adjustable range of motion stop is additionally provided. In a further refinement shown in FIG. 37, only the adjustable range of motion stop is provided. FIGS. 39 and 40 show an alternative construction of the range of motion stop.

Other aspects of the invention will appear from the detailed discussion below. In particular, FIGS. 27-30 show an impact-protective device that can be used with any of the second through fourth embodiments of the joint protective device of the invention, and FIG. 38 shows a preferred multicomponent padding design that can be used with any of the embodiments of the joint protective device of the invention.

BACKGROUND OF THE INVENTION

Horses are large running mammals, typically weighing 450-500 kg (990-1100 lbs), and sometimes much more. They are capable of rapid acceleration and attaining speeds of 20 ms$^{-1}$ (44 mph). Evolution and careful breeding have left horses, particularly horses bred for racing and other athletic contests (as opposed, for example, to draft horses) with comparatively slender and fragile legs comprised substantially of long bones articulated by several series of compact muscles, tendons, and ligaments. The latter three soft tissue structures (as opposed to bone and cartilage, that is) are principally responsible for enabling locomotion either by providing propulsive forces (e.g., upper hind limb musculature), by storing energy (e.g., in the superficial digital flexor tendon ("SDFT"), by abating vibration (e.g., upper forelimb muscles), and by one or more further mechanisms.

The horse's large body size, slender limb structure and occasional need for high speed or rapid acceleration expose the lower limbs, in particular, to risk of injury, either from a single traumatic event such as blunt force trauma or a mis-step of the hoof, or from accumulated micro-damage sustained, for example, during repeated loading of the limb during race training. This can include exposure to too many cycles (frequency) or cycles of excess magnitude (force).

Injury arising from a single incident can affect any of the limb's constituent structures, although the more distal (lower limb) components are generally at greater risk by virtue of their proximity to the ground and ground obstructions. Lower limb structures are placed at greater risk by the paucity of enveloping muscle which, higher up the limb, serves as a 'fleshy' buffer to external trauma. As one progresses toward the foot, the limb is increasingly composed solely of bone and adjacent tendon and ligament fibers covered by skin.

Injury resulting from accumulated micro-damage also has preferred sites of incidence. For example, the dorsal (front) surface of the horse's third metacarpal (cannon) bone or the mid-metacarpal region of the SDFT are locations frequently affected in racing thoroughbreds. In particular, the fetlock joint, at which the cannon bone meets the pastern bone, is extremely vulnerable to injury, often with catastrophic results. The device of the preferred embodiment of the present invention (although as noted the invention is not limited thereto) is directed to reduction of the likelihood of injury to the fetlock, as well as to related anatomical structures that are not part of the fetlock per se, such as the superficial digital flexor tendon and the proximal suspensory ligament, as well as to support of the fetlock during rehabilitation after injury or surgery.

As will be appreciated by those of skill in the art, the corresponding joints in fore and rear legs, and the related structures, are called by the same names as a matter of lay use. In scientific terminology, these names change between fore and hind limb. For example, the fetlock of the forelimb, the metacarpo-phalangeal joint, becomes the metatarso-phalangeal joint in the rear limb. The lay terminology is used herein for simplicity. Again, it will be appreciated that the invention is not thus limited.

It should also be noted that the stiffness of biological, soft tissue structures, including tendons and ligaments, increases at very high rates of deformation. Thus, if the fetlock flexor tendons are stretched very quickly (e.g. due to a misstep or fatigue), they can develop much higher resistive loads than if stretched more slowly, even if the joint is not hyperextended per se. This higher load may lead to injury, especially if it occurs repetitively.

Once sustained, injury—be it to bone or soft tissue—requires substantial periods of complete rest or much reduced exercise before the animal can return to normal activity, and in some cases the recovery is never complete. Man's competitive use of horses—which frequently exceeds 'normal activity'—places additional and frequently unreasonable demands on the healing tissues. As a result, the healing process can be exacerbated and the injury will fail to fully resolve, causing a chronic and sometimes life-long limitation of use. Additionally, while bone is unusual in being able to completely heal itself, soft tissues generally heal with some degree of scar formation which results in added compromise of ambulatory ability, mediated, for example, by pain or adhesions. Scar tissue (unspecialized fibrous tissue in an orientation that is mechanically inferior and/or predisposed to forming adhesions to adjacent structures) is also invariably less strong than undamaged tissue, placing the injured tissue(s) at risk of re-injury.

Recognizing the substantial cost of limb injury to the animal (distress, reduced ambulation, risk of re-injury, etc.) and society (lost use, veterinary bills, investment loss, etc.), researchers have long sought means for reducing the incidence of lower limb injury. Many approaches have been taken including but by no means limited to alteration of ground surface, modification of training techniques, and use of drugs and nutraceuticals. Others have sought to ameliorate the demands placed on the horse's locomotor system during competition by reducing the severity of competitive courses and easing schedules.

Yet another approach has clinicians and researchers attempting to positively impact lower limb biomechanics by limiting extremes of motion, so as to protect both soft and hard tissue structures from being overstressed. The situation is complicated by an incomplete understanding of lower limb mechanics, sometimes resulting in contradictory data findings or theorems. The situation is further exacerbated by the extreme forces occurring within the lower limb during competitive activity—forces which have so far largely precluded the art from preventing extremes of limb motion, for example, by placing the lower limb within protective bandages or boots.

Referring more specifically to the prior art US patents and applications known to the inventors that are directed to protection of the fetlock, and in related fields, Lewis U.S. Pat. No. 121,880 shows a "Stocking for Horses" that is made of rubber and features stiffening ribs to prevent the stocking from working downwardly as the Boise moves.

Hyman U.S. Pat. No. 3,209,517 shows a leg support for horses made of closed-cell foam and secured by Velcro straps.

Pomeranz U.S. Pat. No. 4,471,538 is broadly directed to shock-absorbing devices (not specifically for equine applications) employing "rheoprexic fluid" which appears to generically describe a component of a composite "dilatant" material that is used in some embodiments of the invention.

Boyd U.S. Pat. No. 5,107,827 discloses a protective bandage for the fetlocks of horses that is made of Neoprene synthetic rubber, cut out in a complicated fashion and provided with numerous Velcro strips so that the bandage is secured together at numerous points as it is wrapped around the horse's leg.

Hayes et al U.S. Pat. Nos. 5,545,128 and 5,599,290 disclose methods and garments for reducing bone injury due to impact by provision of "shear thickening", i.e., dilatant, material "in a manner to permit the shunting of impact energy away from the vulnerable [bone] region to the soft tissue region" (claim 1 of the '128 patent).

Walters et al U.S. Pat. Nos. 5,861,175 and 6,368,613 and application 2002/0077368 disclose a method for treatment of articular disorders by injection of fluorocarbons to replace lost synovial fluid.

Chambers U.S. Pat. No. 6,883,466 discloses an animal leg wrap comprising a soft, resilient filler material.

Springs U.S. Pat. No. 6,918,236 shows a breathable equine leg wrap of specific construction. Of interest is the use of phase-change materials for heat removal.

Allen U.S. Pat. Nos. 7,402,147 and 7,789,844 show body limb movement limiters involving a tether paid off a reel, the movement of which is limited by a dilatant fluid.

Greenwald et al U.S. Pat. No. 7,837,640 discloses a joint protective device including an engineered textile including fibers that slide freely over one another at low loads but with increased friction at higher loads, so that the device provides increased resistance to motion at higher loads. The device is also to comprise a "strain rate dependent damping material, so that stiffness in the engineered textile is a non-linear function of displacement, velocity or acceleration". See claim 1. This material can be one exhibiting "dilatant non-Newtonian behavior such that material stiffness increases with strain rate"—see col. 6, lines 40-42.

Bettin et al U.S. Pat. No. 7,896,019 shows control of the viscosity of a dilatant fluid by application of oscillatory stress, e.g., by way of a piezoelectric transducer, so as to tune the material's characteristics to the application.

Clement patent application 2004/0055543 shows a protective device for a horse's leg that comprises a rigid casing and a padded lining.

White patent application 2006/0107909 shows a tendon and ligament support for the legs of a horse that comprises a gel layer, a dry flex layer, and a Lycra outer layer.

Lindley patent application 2006/0231045 shows a horse leg protector comprises an impact-absorbing inner layer of rubber or foam and a rigid outer housing. Ventilating passages are provided throughout.

Heid et al patent applications 2009/0094949 and 2009/0288377 show equine support boots including sling straps providing support to the fetlock.

Farrow et al patent application 2010/0056973 shows a therapeutic compression device to fit around a limb of a patient.

Green et al patent application 2010/0132099 shows "energy absorbing blends" where a dilatant fluid is entrapped in a solid matrix of a polymer material. It appears possible that this application is directed to a material known to the art as "d3o". This material is employed in some of the preferred embodiments of the invention, as discussed in detail below.

Husain patent application 2010/0192290 shows a neck protection collar.

Lutz patent application 2011/0034848 shows a compression bandage for horses involving specific closures.

Eggeman U.S. Pat. No. 2,512,925 shows a skid boot for horses, designed to protect the fetlock from contact.

Dever U.S. Pat. No. 2,937,487 shows a protective leg sheath for horses.

Schubert U.S. Pat. No. 3,193,984 shows an inflatable leg sheath for horses.

Porner U.S. Pat. No. 4,099,269 shows a leg sheath for horses with air pockets built into it for impact resistance.

Shapiro U.S. Pat. No. 4,538,602 shows a spirally-wrapped leg protector for horses.

Scott U.S. Pat. No. 5,115,627 shows a horse boot made up of several specified materials.

Gnegy U.S. Pat. No. 5,152,285 shows a horse boot with pockets for insertion of hot or cold packs to treat the horse's leg.

Amato U.S. Pat. No. 5,363,632 shows a boot with an inflatable bladder to support the underside of the fetlock.

Vogt U.S. Pat. No. 5,579,627 shows a support wrap for a horse's leg, including a fetlock-supporting sling strap.

Vogt U.S. Pat. No. 5,816,032 is a continuation-in-part of the above and claims a tendon support member.

Wilson U.S. Pat. No. 5,910,126 shows a support wrap for a horse's leg.

Farley U.S. Pat. No. 5,441,015 discloses a method for treatment of an injured horse's leg involving a split rigid cast-type device.

Daly U.S. Pat. No. 7,559,910 discloses a device for preventing over-articulation of the fetlock including an articulated joint including a "pivot arrangement". Daly teaches both non-extensible tension members for limiting the range of motion of the joint, which are provided with adjustment to allow different limits on the range of motion, as well as resilient members compressed when the joint is flexed, which would help support the tendons. Daly also suggests that friction could be built into the pivot arrangement.

Rogers U.S. Pat. No. 6,151,873 shows a legging for horses including fly netting.

Bard U.S. Pat. No. 6,553,994 shows an orthopedic support molded so as to provide ventilation channels and passages.

Finally, Detty U.S. Pat. No. 5,871,458 shows an equine ankle brace including a cup-like member for fitting over the fetlock.

As will be apparent, most of the prior art devices shown in the patents and applications mentioned above are simply intended to protect the horse's legs from direct impact damage, which, while doubtless beneficial, is insufficient to protect against damage due to repetitive loading, overexertion, hyperextension of the joint, and the like. These damage mechanisms are discussed more fully below. Of the art discussed above, only the device shown in the Daly patent is explicitly intended to prevent hyperextension by mechanical means.

More specifically, it is an object of the present invention to provide a device that provides actual mechanical support to the fetlock, in essence providing additional support to the articular interface, joint capsule, tendons, ligaments, and other periarticular structures without unduly interfering with the normal motion of the joint. Still more particularly, according to one aspect of the invention, a joint supporting device is provided that comes into play primarily as the horse fatigues, for example, towards the end of a race, when it is most vulnerable to damage. Several different and complementary ways in which this can be accomplished are disclosed herein. In other embodiments of the invention, a joint support device is provided intended primarily for rehabilitation after surgery or injury, where fatigue per se is less significant.

Referring now to the typical damage mechanisms experienced by horses, injuries resulting from accumulated micro-damage, which from a clinical perspective are equally if not more prevalent than injuries from a single traumatic event, have predilection sites, which are in turn linked to specific athletic activities. For example, the superficial digital flexor tendon (SDFT) in the mid to proximal metacarpal region of the front limb is the most frequently injured locus in racing thoroughbreds while the suspensory ligament (SL) is more frequently injured in racing standardbreds. Deep digital flexor tendon (DDFT) injury is most commonly encountered in jumping horses while hind limb proximal suspensory injury is more common in dressage horses. Similarly, bone and cartilage injury secondary to accumulated microdamage have predilection sites, for example, the proximal-dorsal aspect of the first phalanx within the fetlock joint. In each case, the likelihood of injury appears to increase with fetlock hyperextension, that is, extension of the joint beyond its normal range of motion.

Referring now specifically to the equine fetlock, within that region lie three particularly 'at-risk' principal soft tissue support structures (the SDFT, the DDFT and the SL) on the palmar/plantar (back) aspect of the bones, which work in unison with the limb's many other soft tissue components (e.g., the joint capsule, annular ligaments, and extensor tendons) to effect locomotion.

To best understand how the current invention will prevent injury to the SDFT, DDFT and SL, their anatomical and functional characteristics will be reviewed.

Collectively, the SDFT, DDFT and SL are substantially modified muscles, possessing short muscle fibers, a pennate structure (that is, comprising a muscle in which fibers extend obliquely from either side of a central tendon) and significant passive elastic properties. The SL, an evolutionary modification of the interosseus muscle, is completely fibrous with only remnants of muscle fibers to be found. The superficial digital flexor muscle (proximal to but contiguous with the SDFT) is also almost completely fibrous in the hind limb and in the forelimb has short muscle fibers of 2-6 mm length. These are primarily 'slow' muscle fibers best suited to supportive rather than propulsive functions by means of constant or extended length activity. The deep digital flexor muscle has three heads or muscle compartments (humeral, radial and ulnar) composed of varying numbers of short, intermediate, and long muscle fibers. It combines slow muscle fibers with a substantial population of 'fast' fibers which are better suited to propulsive functions. The SDFT and DDFT muscles are protected by accessory ligaments that link the tendon, distal to the muscle belly, to bone, effectively protecting the muscle and limiting the overall stretch (strain) that can be effected through the structure.

Once a horse has expended substantial energy in accelerating to a constant speed, a primary goal is to maintain that speed while minimizing the subsequent use of energy. The SDFT and DDFT have a major role in this process wherein their largely tendinous composition allows them to store and then return elastic energy, in the manner of a spring being stretched to store energy and then released to expend the stored energy. The SDFT and DDFT do this with remarkable efficiency, returning about 93% of the energy stored, much of the rest being dissipated as heat.

During the energy storage process at the time of weight-bearing, the tendons are substantially stretched. Under normal circumstances, the amount of stretching which they sustain (which may be as much as 8-12% of the resting length) remains within physiologically normal limits, allowing the tendons to recover their original form without injury. This elastic increase in length is the very means by which energy is efficiently stored in the same way that a spring stores energy by stretching, as above.

However, during extremes of activity the tendon or ligament can be stretched so much, particularly as the horse fatigues, that micro- and sometimes macro-damage occurs.

Progressive degenerative changes within the tendon or ligament may precede and predispose to this injury. Given sufficient recovery time, micro-damage can often be repaired. If not, micro-damage can accumulate leading to macro-damage. The dividing line between the tendon strains (that is, the amount by which it is stretched) required to achieve efficient elastic energy storage and those which result in disruption of the tendon microstructure is very fisc. If disc uptiun does occur but is limited to a very small volume, the damage can be accommodated without compromising function, but when the injury is more widespread, clinical unsoundness can result.

At rest the SL is fully capable of passively resisting change in fetlock angle. At speed, however, the SDFT and DDFT provide additional support for the fetlock, countering the substantial weight-bearing forces, which tend to hyperextend the joint. A controlled increase in joint extension is preferred. Towards extremes of exertion, however, the fast muscle fibers of the DDFT become fatigued and, with the passive SL limited in its ability to provide additional support as determined by its architecture, the SDFT is increasingly responsible for countering hyper-extension of the fetlock. Eventually, the SDFT can also be overloaded, the joint progresses to hyperextension, and damage ensues.

The SDFT and DDFT have additional roles, including the damping of the high-frequency (30-50 Hz) vibrations that occur at foot impact and which otherwise would cause increased onset of structural fatigue damage within bone and soft tissue, by increasing the number of loading cycles and the loading rate experienced by the limb.

Other comments regarding modes of injury include the following:

In addition to injury of the principle flexor soft-tissue structures (SL, SDFT and DDFT), fetlock hyperextension can also cause injury of hard tissue structures of the lower limb. For example, with fetlock hyperextension, the increasing forces exerted on the cartilage and underlying bone of the dorsal peripheral margin of the fetlock joint can cause microfracture. If given insufficient time to heal, accumulated microdamage eventually results in clinical injury caused, for example, by cartilage cracking and associated osteoarthritis or even bone fracture.

While the etiology (i.e., cause) of some SDFT, DDFT, and SL injuries are better understood than others, the final common pathway is one of mechanical disruption of collagen, the principal component of tendon and ligament, at a microscopic and sometimes macroscopic level. Concurrent with the disruption of the individual collagen fibers or bundles of fibers is local bleeding and resultant inflammation. Clinically this is characterized by pain, heat and swelling. The blood clot is subsequently resorbed and/or replaced by new collagen fibers laid down in a new extracellular matrix (bed), initially in random configuration. Finally, the collagen undergoes remodeling and is realigned to best offset the loading forces extant at that location. The process in its entirety takes up to one year to complete. As stated previously, the scar tissue thus formed is generally inferior in its mechanical qualities to uninjured tendon, predisposing the limb to reinjury.

Which of the support structures of the limb that is injured in any particular case, and where the injury might occur along its length, is predicated on multiple factors including but not limited to blood supply, pre-existing injury, degenerative disease, point of focal loading, activity type and quite possibly a series of mechanical parameters with pertinence to joint dynamics as well as the visco-elastic nature of tendons and ligaments.

It will be apparent that to the extent the fetlock joint can be prevented from being hyperextended, loading the support structures beyond their normal elastic limits, and possibly also causing hard tissues from experiencing excessive compression stress, injury to both soft and hard tissue can be limited. Intuitively, limiting extremes of fetlock motion would appear to be most easily achieved by physically restricting the upper limits of flexion and particularly extension in the longitudinal axis (forward and backward). Various types of boot and bandage have been studied with this goal in mind in previous reports. The data is often contradictory. Crawford et al. (1990a,b) found that different bandaging techniques and materials significantly influenced the energy absorption capacity of these bandages. Keegan et al. (1992) showed that support bandages did not alter mean strain in the suspensory ligaments while the horses were standing or walking. Using a tensile testing machine, Balch et al. (1998) demonstrated in an in vitro setting that certain types of support boots could absorb up to 26% of total force. However, in a similar set-up, Smith et al. (2002) found no difference between limbs with and without neoprene support boots. Kicker et al (2004) found some support boots to provide a significant reduction in total joint extension of up to 1.44 degrees at the trot, the practical implications of which have yet to be determined. Ramon et al (2007) found that athletic taping of the fetlock did not alter the kinematics of the forelimb during stance, but does limit flexion of the fetlock by approximately 5 degrees during the swing phase. A decreased peak vertical force also resulted, quite possibly due to an increased proprioceptive effect. Finally, Swanstrom (2005) shows soft tissue strain with fetlock angle for SDFT, DDFT and SL.

The present inventors estimate from this data that limiting the fetlock extension by 8 degrees is required to achieve a 10% reduction in extension of the SDFT, DDFT, and SL.

Similarly, it will be intuitively apparent that limiting the angular velocity of the joint—that is, the rate at which the joint is moved between extension and flexion—will be useful in preventing injury. More specifically, increasing the load rate on a visco-elastic material such as soft tissue increases the stiffness of the material, that is, increases its resistance to stretching. This in turn may increase the likelihood of the tissue tearing. Conversely, reducing the angular velocity implies that one is probably (though not definitely) reducing the load rate. With viscoelastic tissues, this will make them less stiff and thereby they should offer less resistance to load and hence they should experience less likelihood of tearing.

The objects of the invention are therefore to address the following biomechanical protection strategies. As will become apparent from the discussion of the several embodiments of the device of the invention described below, not all of the embodiments are directed toward each of these points.

1. Limitation of longitudinal or mediolateral ultimate joint flexion or extension, that is, limitation of the range of motion of the joint;
2. Limitation of longitudinal or mediolateral rate of joint flexion or extension, that is, limitation of the angular velocity of the joint;
3. Limitation of flexor apparatus ultimate load, that is, limitation of the loading experienced by the tendons and associated structure;
4. Limitation of flexor apparatus load rate, that is, limitation of the rate at which the tendons and associated structure are loaded;
5. Re-distribution of ground reaction forces away from bone to more superficial soft tissues.

6. Dissipation of ground impact-derived concussive forces.

Furthermore, it is important that these be accomplished without adversely affecting the horse's proprioceptive ability, while interfering with the horse's normal motion as minimally as possible, and while limiting overheating of the joint insofar as possible.

SUMMARY OF THE INVENTION

As mentioned above, the joint supporting device of the invention is disclosed in several distinct embodiments, having differing intended uses and therefore different characteristics. These will be explained in the following. Further, as also mentioned above the invention is described in connection with support of the equine fetlock, but is not limited thereto.

According to a first embodiment of the invention (see FIGS. 5-13a and 16), a fetlock-supporting device is provided comprising tensile members which serve to add additional tensile capability, supplementing the tensile characteristics of the SDFT, DDFT, and SL. The tensile members extend between a proximal cuff above the fetlock to a distal cuff at the hoof, and pass over a fetlock pad at the rear of the joint, redirecting the tensile members. In this embodiment, the proximal and distal cuffs are not joined to another for relative motion as the joint is flexed and extended. Therefore, in order that the cuffs are supported in position, so that the tensile members can effectively support the joint, the cuffs are spaced away from the joint by compression members bearing on proximal and distal bolsters, in turn located positively by the boney structure of the fetlock. In this way the tensile members can effectively support the fetlock without the need for constricting cuffs, which would be painful and tend to reduce blood circulation if made tight enough to be effective as anchors for tension members.

As mentioned, when the device is to be used while the horse is exercised, it is important that the structure of the invention not interfere overly with the normal function of the fetlock, but provide support when the horse fatigues and is most susceptible to injury of any or all of the SDFT, DDFT, and SL, as well as the bone and cartilage structures of the joint. There are several ways in which this can be accomplished, all of which are considered to be within the scope of the invention. One comprises use of dilatant materials, which have the property (as discussed briefly above) of varying their resistance to shear responsive to shear force. More specifically, there is now available a material known as "d3o", which comprises a dilatant fluid confined in a matrix of a polymer, so that the dilatant fluid can be disposed as needed. In the present context, the dilatant material is disposed so as to prevent further motion if the angular motion of the fetlock becomes too rapid, or if its range of motion becomes close to hyperextension, either of would tend to occur during transient instabilities or missteps or as the horse fatigues, or possibly in the case of an unfit or poorly muscled horse. The dilatant material can be disposed as the core of a composite tension member, sheathed in a cover woven of high tensile strength filaments or yarns.

In a further embodiment, the dilatant material can be controlled responsive to an external signal. For example, the range and rate of angular rotation of the fetlock can be monitored as the horse exercises, for example, in a race, and compared to reference values for safe exercise determined during testing. Where the rate and/or range of fetlock angular rotation approach unsafe levels as the horse becomes fatigued during exercise, the dilatant material can be controlled to become stiffer (possibly using the piezoelectric technique disclosed in the Bettin et al patent discussed above) and thereby resist hyperextension of the joint, to avoid injury.

In other embodiments of the invention (see FIGS. 17-21, 22-26 and 31-40), the proximal and distal cuffs, bolsters and compression members of the embodiment described briefly above can be replaced by proximal and distal cuffs which are joined to define an axis of rotation coaxial with the anatomical joint. Resilient members extending between the proximal and distal cuffs can be employed to provide additional load-bearing capability, useful to prevent injury during exercise. The angular velocity of the joint can also be restricted. Further, in additional embodiments, the range of motion of the joint can be restricted, which is particularly useful in rehabilitation of the joint after injury. Further aspects of the invention will become apparent from the detailed discussion below.

BRIEF DESCRIPTION OF THE DRAWINGS

The invention will be better understood by reference to the accompanying drawings, in which:

FIGS. 5 and 6 show, respectively, side and rear views of the device of the invention illustrating key structural components thereof;

FIG. 7 shows one way in which tensile members comprised by the device of the invention can be affixed to cuffs thereof, and FIG. 8 shows a detail thereof;

FIGS. 9 and 10 show respectively elevation and side views of a ratchet-and-pawl mechanism for adjusting the tension in the tensile members;

FIG. 11 shows a more detailed rear view of the device of the invention;

FIG. 12 shows another means for affixing the tensile members to the cuffs;

FIG. 13 shows a detailed side view of a fetlock pad comprised by the device of the invention;

FIG. 13A shows a cross-section along the line 13A-13A of FIG. 13;

FIGS. 14 and 15 show, respectively, side and rear views of a goniometer to be affixed to the leg of the horse for measuring fetlock angle as the horse moves;

FIG. 16 shows a composite tensile member;

FIG. 17 shows a left-side view of a second embodiment of the device of the invention;

FIG. 18 shows a rear view of the embodiment of FIG. 17;

FIG. 19 shows a front view of the embodiment of FIG. 17;

FIG. 20 shows a left-side perspective view comparable to that of FIG. 17, with external structure removed to show underlying details;

FIG. 21 shows an elevational view of a tensile member used in the embodiment of FIG. 17;

FIG. 22 shows a left-side view of a third embodiment of the device of the invention;

FIG. 23 shows a front view of the embodiment of FIG. 22;

FIG. 26 shows a top view of the embodiment of FIG. 22;

FIGS. 27-29 show an optional "run-down" preventer that may be added to the device of the invention in various embodiments; it is shown in connection with the embodiment of FIGS. 22-26, the run-down preventer being shown in different positions in FIGS. 27-29 depending on the degree to which the fetlock is extended;

FIG. 30 shows a cross-sectional view taken along the line 30-30 of FIG. 29;

FIG. 39 is a view comparable to FIG. 35, showing an alternative construction; and FIG. 40 is a cross-sectional view taken along the line C-C of FIG. 39.

DESCRIPTION OF THE PREFERRED EMBODIMENTS

Figures 1, 2:
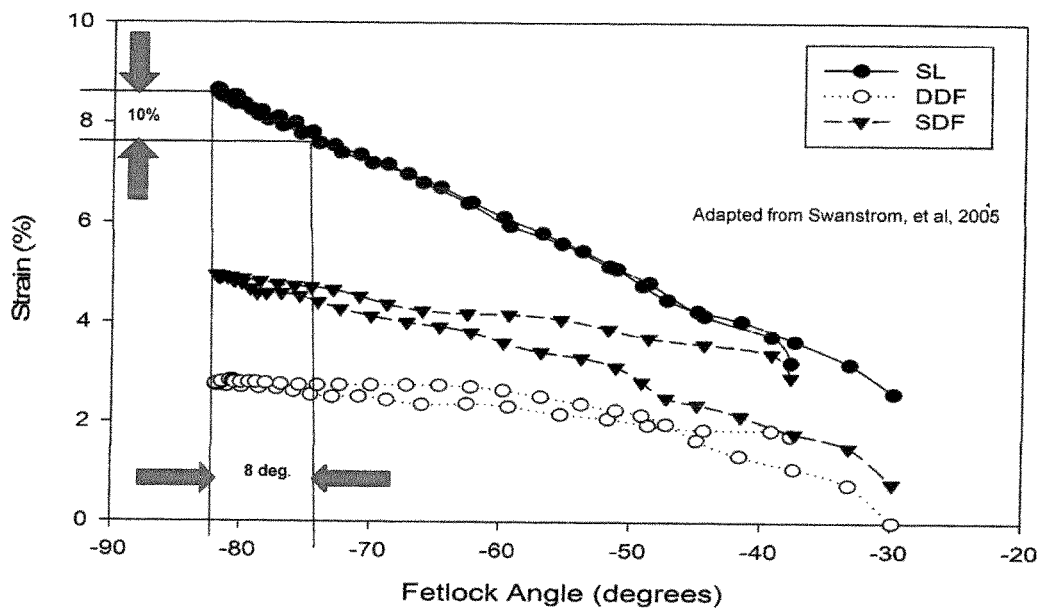
FIG. 1 shows a graph of fetlock angle versus strain in the SL, DDF, and SDF structures discussed above.
FIG. 2 shows schematically the way in which the device of the invention is intended to increase the natural spring constant provided by the stretch in the SL, DDF, and SDF structures.

FIG. 1 shows the strain experienced by the SL, DDF and SDF as the fetlock is extended during the weight bearing phase of gait. As above, the available data indicates that an eight degree reduction in fetlock angle is required to achieve a ten percent reduction in peak tendon strain. Achieving this eight degree reduction in fetlock extension is accordingly one of the desired design goals of the invention. Along with this reduction in peak fetlock angle, the peak angular velocity can also be reduced accordingly. The peak angle can be reduced by limiting the range of motion of the joint, and in some embodiments by adding a parallel load path having the capability of storing and releasing energy, reducing the necessity for the fetlock's structures to store energy, thereby increasing the overall stiffness of the fetlock joint. Specifically, fetlock stiffness will be increased toward the end of its extension.

FIG. 2 shows the approach schematically: The device adds another spring structure in parallel with the SL, DDF and SDF, increasing the effective spring constant experienced by the fetlock, and thereby limiting its maximum extension in response to a given force applied. The device function can be fine tuned in order to control the device stiffness, in particular to achieve non-linear increase in resistance to motion and limitation of angular velocity as the joint becomes fully-extended. Use of both elastic and viscoelastic elements will allow a close match to the normal fetlock stiffness, that is, as exhibited without a device.

More specifically, the first embodiment of FIGS. 5-13$a$ and 16 employs a dilatant material to increase resistance to motion as the angular velocity of the joint increases, and can also be configured to limit the range of motion of the joint. In the second, third and fourth embodiments of the invention, as shown in FIGS. 17-21, 22-26, 31-36, 39 and 40 respectively, the device comprises supplemental energy absorbing members; in some embodiments the range of motion of the joint is also limited. Finally, the embodiment of FIG. 37 simply limits the range of motion of the joint, without the additional energy absorbing members of the embodiments of FIGS. 17-21, 22-26, 31-36, 39 and 40.

Figure 3:
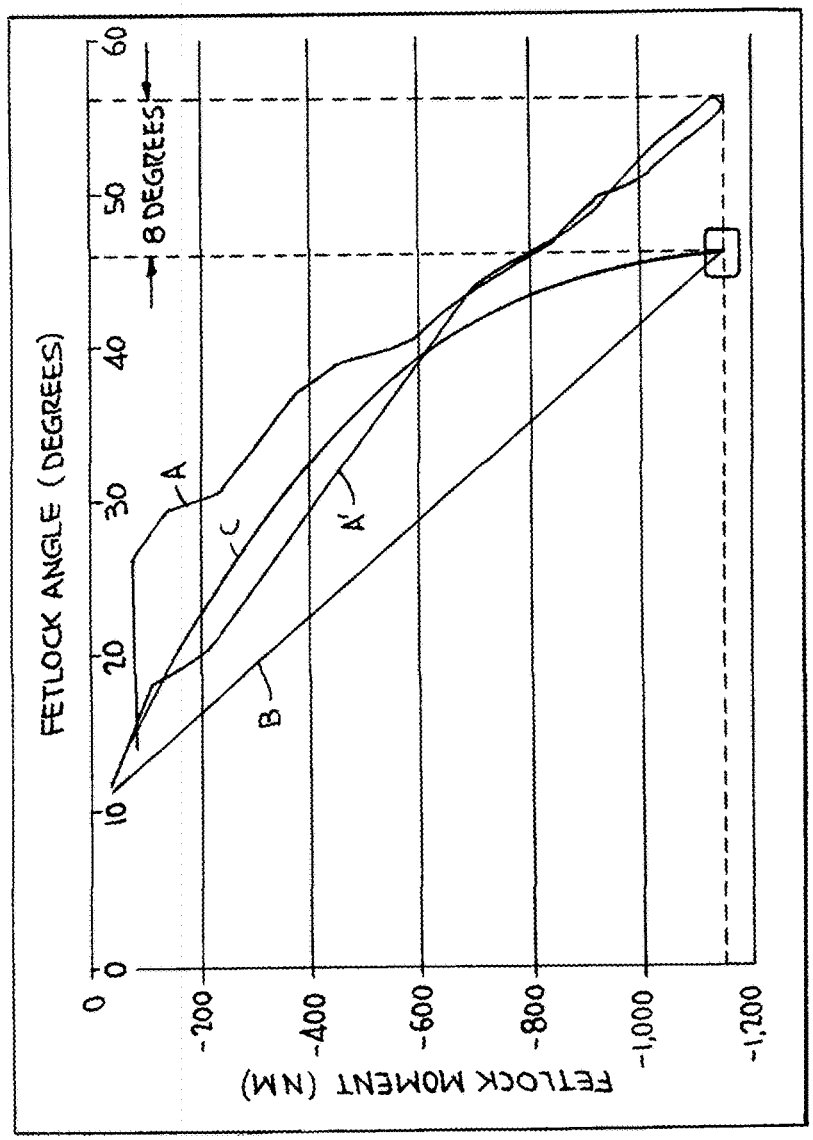
FIG. 3 shows the fetlock moment in Newton-meters as a function of fetlock angle, and illustrates the manner in which the device of the invention is to operate to limit the maximum extension of the fetlock.

FIG. 3 shows graphs of fetlock maximum angle versus the moment (i.e., torque applied). The curves marked A and A' show measured data for fetlocks with no additional device provided; as noted above, in this particular case the joint can operate up to about 56 degrees of extension. In order to limit damage, it is desired as above to limit this to about 48 degrees. This absolute angle may vary from animal to animal, of course, and the individual examples of the device of the invention will be able to accommodate changes to this preferred angle. The curve marked B shows performance with linear increase in stiffness with angle and curve C shows performance with a non-linear increase in stiffness. Both devices achieve the desired eight degree reduction in fetlock extension, but the non-linear stiffness device of curve C will allow more normal motion until the fetlock reaches hyperextension. Accordingly, a primary goal of the present invention is to provide non-linear increase in additional energy absorption capability with extension of the joint, so as to allow normal fetlock motion insofar as possible while restricting pathologic hyperextension, and likewise to limit the maximum rate of joint rotation without unduly restricting motion.

Figure 4:
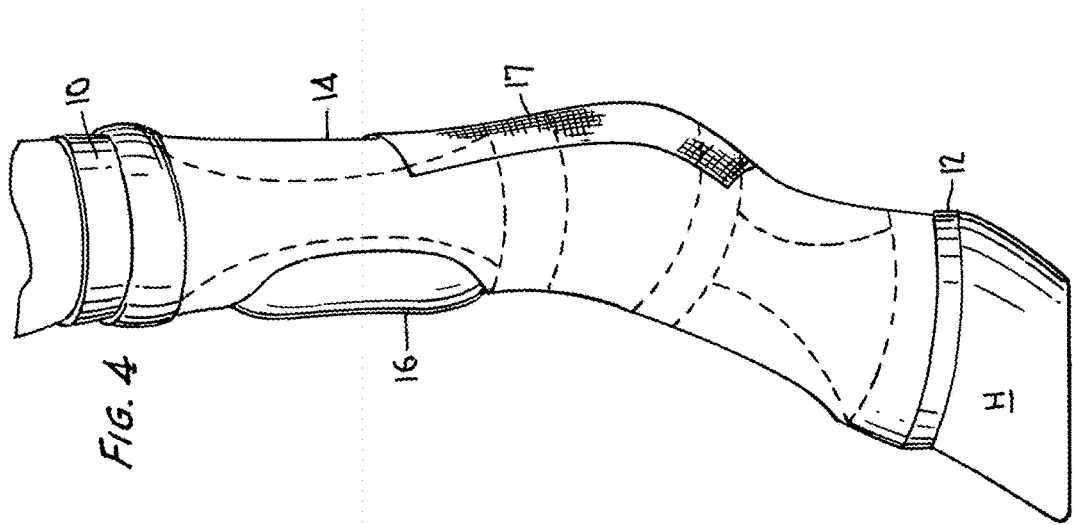
FIG. 4 shows the external features of a first embodiment of the device of the invention, in a side view.

Another goal of the present invention is to protect the fetlock region from impact damage, to provide cooling and moisture wicking insofar as possible, to damp vibration, and to provide abrasion resistance to the fetlock. FIG. 4 shows the outer structure of the device according to the first embodiment of the invention, which provides these features. The structural elements that are directed to the other objects of the invention mentioned above are disposed within the outer structure of FIG. 4, or between inner and outer sleeves thereof, and are discussed more fully below.

Thus, as illustrated in FIG. 4, the device of the invention comprises an inner sleeve 10 made of a moisture-wicking breathable material (such as that known as Coolmax, or possibly that known as X-static) extending the length of the device, which is shown in use, that is, installed over a horse's fetlock. The lower end of inner sleeve 10 is terminated by an elastomeric seal 12, sealing sleeve 10 to the upper portion of the horse's hoof H, to prevent entry of dirt, sand, and moisture. An outer sleeve 14 is also provided of a breathable, lightweight, durable elastic material (such as that known as Drytex). A protective pad 16 of a viscoelastic material (such as that known as Sorbothane) is provided on the forward portion of the cannon bone, for vibration damping. Pad 16 can be secured to either the inner sleeve 10 or outer sleeve 14. Similarly, a protective member of abrasion resistant textile 17 can be provided on the rear of the fetlock, to protect the joint in case of "rundown", where the fetlock is hyperextended so far that the rear of the fetlock contacts the ground.

FIGS. 5 and 6 show the principal components of a first embodiment of the device of the invention which serve to strengthen and stiffen the fetlock joint. These include a proximal cuff 20, a distal cuff 22, a proximal fetlock bolster 24, a distal fetlock bolster 26, a fetlock pad 28 over the proximal sesamoid bones, proximal and distal compression members 30 and 32, and tensile members 34 connecting the proximal and distal cuffs 20 and 22 and passing behind the fetlock pad 28.

As mentioned above, one of the primary objectives of the structure of FIGS. 5 and 6 is to limit the degree to which the fetlock joint can be extended, which occurs in the direction of arrow D in FIG. 5; that is, as the horse runs, and the hoof hits the ground, the fetlock rotates in the direction of arrow D, stretching the tendons, ligaments, and muscles. When the collective strength of the muscles and tendons equal and then exceed the opposing forces, they pull the fetlock back toward the static position shown in FIG. 5. In this way the horse's leg exerts force on the ground, propelling it forward.

As mentioned above, hyperextension of the fetlock is to be prevented—that is, the range of motion of the joint is to be limited—by the structure shown. This requires that the tensile members 34 carry tension from the distal cuff 22 to the proximal cuff 20. As the proximal and distal structures are not fixed to one another by means allowing for relative rotation, it will be apparent that in order to do so the cuffs must be retained in their respective positions. It would not be desirable to make the cuffs fit so tightly that friction alone would hold them in place, as this would require so much clamping pressure as to be very uncomfortable for the horse and impede blood circulation.

Therefore, according to an important aspect of the invention, the proximal and distal cuffs 20 and 22 are retained in position by respective compression structures 30 and 32 bearing against respective bolsters 24 and 26. Bolsters 24 and 26 are in turn retained in position by bearing against the boney anatomy of the fetlock, which is sufficiently non-uniformly cylindrical that properly-fitted bolsters will not tend to be drawn toward one another by tension in the tensile members 34. The cuffs, compression structures, and bolsters can be adhesively bonded to one another, e.g., in an initial fitting of a particular device to a particular horse, or the assembly can be provided in a variety of sizes to suit different horses.

Thus, as the horse runs, and the fetlock is repeatedly extended and relaxed, the tensile members 34 will be repeatedly tensioned and released. (The degree to which tensile members 34 are tensioned will depend on the degree they are tensioned at installation of the device; this can be made adjustable in a manner discussed below.) Tension from the tensile members 34 is taken up by the cuffs, which are accordingly urged toward one another. The relative motion of the cuffs is resisted by the compression structures, in turn supported by the bolsters, in turn spaced apart by the boney structure of the fetlock.

The tensile members 34 are arranged so as to pass over the rear of the fetlock pad 28. This may comprise a molded thermoplastic saddle against which the tensile members 34 bear, with a resilient or dilatant member between the saddle and the skin over the fetlock. Presently preferred structures of the fetlock pad is shown in detail by FIG. 10 and FIGS. 13 and 13A. In this way the direction of the tension in the tensile members 34 is redirected around the rear of the fetlock, from the proximal cuff 20 to the distal cuff 22, generally parallel to the orientation of the tendons and ligaments.

The tensile members 34 comprise elongated filaments, strands or yarns of light, flexible material of high tensile strength, such as a liquid crystal polymer material, one example of which is commercially available as Vectran. It will be appreciated that this material is not resilient; that is, this material does not stretch under load, and does not store energy. Instead, the function of the tensile members in this embodiment of the invention is to limit the range of motion of the joint. FIG. 16 shows a preferred construction of these tensile members, also incorporating dilatant material.

FIGS. 7 and 8 show one way in which the tensile members 34 can be secured to the proximal and distal cuffs 20 and 22 in order that the tension in tensile members 34 can be transferred to the anatomy of the horse and thus effectively help to support the fetlock. The high point loads occasioned by the attachment of such slender members to a cuff can be accommodated as illustrated.

The cuffs (proximal cuff 20 in the illustration) will comprise an outer shell 40 of a relatively hard material lined with a pad 42 of a resilient material so as not to irritate the horse's skin. A molded thermoplastic outer shell 40 lined with a pad 42 of a material such as that sold as Sorbothane may suffice. The constraint is that the outer shell 40 of the cuff 20 must be C-shaped and have sufficient flexibility to be able to be temporarily deformed and slipped over the horse's leg from the front or over the hoof, from below. The two ends of the "C" can then be affixed to one another by a buckle, snap fitting, "Velcro" or the like. See FIG. 11. The structure of distal cuff 22 is similar. The structure of the bolsters 24 and 26 will be generally similar, although these of course will not require terminations for tensile members. The compression structures will likewise comprise an outer shell molded of a relatively hard material, lined with a resilient pad.

As shown, the outer shell 40 may be molded to comprise one or more recesses 44 with surrounding lips 46 to retain a ball 48 crimped on to the end of a strand 50 of the tensile member 34. A generally tubular grommet or interface member 49 (FIG. 8) of resilient material, possibly having metallic washers (not shown) on either side, may be interposed between the shell and ball; as tension is applied to the tensile member 34, this grommet 49 will compress, further tensioning the tensile member 34 and restricting overall movement and angular velocity of the fetlock. Grommet 49 may also be formed of dilatant material, hardening as it is compressed by tension applied by the tensile member 34, so as to increase tension in the tensile members 34 in a non-linear fashion.

Numerous other means of terminating the strands 50 of the tensile members 34 to the cuffs are within the skill of the art. For example, numerous smaller strands of the tensile material could be wrapped in a separate operation around metallic end fittings, so that the individual strands do not themselves experience excessive tension; the end fitting might then be riveted to the outer shell 40 of the cuff. FIGS. 11 and 12 show an alternative where the tensile members are wrapped around the cuffs, largely avoiding the problem of terminating the tensile members at the cuffs. Various specific orientations of the tensile members are also within the scope of the invention, as illustrated.

FIGS. 9 and 10 show one possible method of adjustment of the tension of the tension members between the proximal and distal cuffs. Here, the fetlock pad assembly 28 comprises a member 56 of material chosen to harden when subjected to compression loads, such as the material known as d3o, which, as above, comprises a dilatant polymer confined in a matrix of a closed-cell polymer. This material (which may be encased in a further sheath (not shown) of a friction-reducing material (e.g., that sold as Spandex)) contacts the horse's fetlock. Affixed to this member 56 is a molded plastic saddle member 58. An internally-toothed gear 62 is molded integrally with saddle member 58. A take-up spool 60 is pivoted to saddle member 58 at 64. A pawl 66 is spring-biased outwardly with respect to, and is carried by take-up spool 60, so as to engage the teeth of gear 62. Tension members are wound around the take-up spool 60 from opposite sides, as shown.

Thus, when spool 60 is rotated in the counter-clockwise direction (in the view of FIG. 9), the tension members are drawn onto spool 60, tightening the tension therein. The pawl 66 interacts with the gear 62 to retain the desired tension. This can be done upon initial fitting of the device to the horse, or upon each use. Other methods of adjusting the tension of the tensile members are within the skill of the art.

FIG. 11 shows a rear view of one preferred embodiment of the device of the invention, providing additional details. As previously, the tensile members 34 connect the proximal cuff 20 to the distal cuff 22, while the compression members 30 and 32 space the cuffs from the respective bolsters 24 and 26. In this embodiment, as shown further by FIG. 12, the tensile members 34 are wrapped around the cuffs, avoiding the necessity of fixing points as described above, and pass through channels or tunnels formed on the rear of the fetlock pad assembly 28. As indicated at 70, the cuffs and bolsters can be secured in place over the horse's leg by buckles, snaps, Velcro, or the like. With the tensile members slack, the cuffs and bolsters will be "opened" (as one spreads open a tight fitting shoe to insert one's foot), allowing the device to be slipped over the hoof and slid up the leg into position.

FIGS. 13 and 13A show further details of the fetlock pad assembly 28, and illustrates an embodiment differing somewhat from that of FIG. 10. As illustrated, the fetlock pad assembly 28 may comprise a saddle member 29 molded of a hard plastic material, having grooves 29a or tunnels (not shown) molded therein to receive the tensile members 34. A dilatant pad 31 is affixed to saddle member 29, e.g. by cooperating hook structures (not shown). Dilatant pad 31 may comprises a deformable container 31a containing a quantity of the dilatant material, e.g., the d3o material discussed previously. As shown, the dilatant pad 31 may be of generally toroidal or "donut" shape, to better fit over the fetlock, and specifically to fit over and provide support to the sesamoid bones.

As the horse runs, as noted, the tensile members 34 will repetitively become increasingly taut, and will then be relaxed. As the tension in tensile members 34 increases, the pad member 56 (or 31, in the embodiment of FIGS. 13 and 13A) will be under increasingly more compression. Due to the properties of the dilatant material, as the pad 56 (or 31) is increasingly rapidly compressed, it effectively stiffens. Similarly, if grommet 49 is provided and made of the d3o material, it will likewise repetitively become harder upon each stride, as the horse runs. Accordingly, as the horse runs and becomes fatigued, so that its own tendons stretch, and the fetlock becomes more extended, or if the joint is hyperextended for some other reason, the d3o material will be increasingly compressed, and will become stiffer.

In this way the device of the invention provides increasing tensile support to the fetlock as the horse becomes fatigued, providing more support against hyperextension of the fetlock, e.g., as the horse fatigues. Providing the fetlock pad with the dilatant material as described would also serve to limit the maximum angular velocity of the fetlock; as the dilatant material is deformed by compression of the tension members, it stiffens, limiting the angular velocity of the fetlock. Further, the structure shown will provide additional support to the fetlock in a non-linear fashion; that is, while the horse's fetlock motion is normal, the device of the invention will interfere minimally with its normal motion, but as the horse fatigues, the device will exert more and more resistance to limit both the range of motion and the angular velocity of the joint, preventing injury from both hyperextension and excessive angular velocity.

Another method of limiting the angular velocity of the fetlock which seems very promising is to provide the dilatant material in a polymer matrix as the core of a small-diameter composite tension member, with this core being sheathed in a braided cover made of yarns of high-tensile strength flexible material, such as the Vectran liquid crystal polymer discussed above. This composite tension member could be used as the tensile members 34 of the device of the invention, as discussed above.

For example, as shown schematically in FIG. 16, the dilatant material 90 could be contained in a series of small tubular compartments 92 formed by crimping a tube 94 of a polymer under conditions of heat and pressure so as to seal the compartments. This assembly could then be sheathed in a braided cover 96 woven of a high-tensile yarn, e.g., of the Vectran material discussed above. As tensile members 34 of this construction are placed under increasing tension as the horse runs, the braided cover 96 would be reduced in diameter, compressing the dilatant material 90 and stiffening the tensile member. Likewise, as the tensile members 34 bend over the back of the fetlock pad, the dilatant material will be further stiffened. This stiffening of the tensile members, particularly as they pass over the back of the fetlock pad, would prevent the fetlock from excessive angular velocity.

It will be appreciated that tensile members 34 of this construction as essentially non-resilient, that is, they do not themselves provide an energy-absorbing function. They instead serve to limit the range of motion of the joint, that is, provide a range of motion stop. The dilatant material may provide some energy absorption. Alternatively, the tensile members could be made of a resilient material, in which case they would serve to absorb energy and help take the load otherwise experienced by the tendons and related body structures.

FIGS. 14 and 15 show a goniometer, that is, a device for measuring angles, which can be attached to the horse's leg for measuring fetlock extension. The goniometer can be used in a first stage for determining the horse' normal range of motion (ROM), and, in one possible embodiment, for limiting the ROM to prevent injury. The goniometer comprises first and second arms, 80 and 82 respectively, that are attached to the cannon and pastern part of the leg, that is, above and below the fetlock. Arms 80 and 82 are joined at a pivot point 84 arranged to be aligned with the joint of the fetlock. A potentiometer 86 is arranged to have its body fixed to one of arms 80 and 82 and its shaft to the other, so that as the horse moves the resistance of the potentiometer 86 varies as the angle of the fetlock. The potentiometer is connected to a data logger (not shown) by wire 88, so as to collect fetlock-extension data as the horse exercises.

For example, the horse can be exercised on a treadmill to determine its normal ROM. This data can be used to optimize the tension in the tensile members to limit the ROM. In a further embodiment, the goniometer can be worn by the horse when exercising and normal ROM data compared with ROM data collected during exercise and used to limit the ROM accordingly as the horse fatigues, by altering the dynamic characteristics of the device and reduce the chance of injury. This can be accomplished by stiffening the dilatant material in response to an external signal, as suggested by the Bettin et al patent, discussed above. This could possibly also be combined with the "engineered textiles" of the Greenberg et al patent discussed above; these use a "viscoelastic" material that comprises some degree of "springiness" in that it can store and release energy, as a spring does.

As mentioned above, FIGS. 17-20 show a second embodiment of the device of the invention, while FIG. 21 shows a detail of a tensile member used to provide additional energy storage, reducing the loads on the tendons and associated structures of the joint, as described above in connection with FIG. 2.

In this embodiment, the device 100 is shown in the left-side view of FIG. 17 over an equine fetlock, shown in phantom; in FIG. 18, from the front; in FIG. 19, from the rear, and in FIG. 20, in a perspective view from the left side as in FIG. 17, but with outer structure removed to illustrate the underlying structure.

As shown, device 100 includes two upper cuffs 102 and 104, disposed above the fetlock, and secured thereto by straps 110, 112, 114, and one saddle member 106 secured below the fetlock by a strap 116. Cuffs 102 and 104, and saddle member 106 may be molded of tough plastic material and provided with suitable interior padding, e.g., of the Sorbothane material mentioned above. Upper cuffs 102 and 104 are secured by fasteners 108 (see FIG. 20) to left and right-side upper pivot members 120 and 122, which may be fabricated of aluminum or a like rigid, lightweight material. Thus, in this embodiment the lower cuff 104 is spaced from the upper cuff 102 by pivot members 120 and 122. Saddle member 106 is formed integrally with (or could be assembled rigidly to) left and right lower pivot members 124 and 126. The upper pivot members 120 and 122 are pivoted with respect to lower pivot members 124 and 126 at opposed pivot joints 128 and 130, such that as the fetlock extends, in the direction of arrow A in FIG. 17, the saddle member 106 pivots with respect to the upper pivot members 120 and 122, and thus with respect to cuffs 102 and 104. Pivot joints 128 and 130 are located so as to be substantially aligned with the axis of pivoting of the fetlock.

As the fetlock extends, resilient members 132, fixed at upper ends thereof 132a to upper pivot members 120 and 122 and at lower ends thereof 132b to lower pivot members 124 and 126, are extended and stretch, thus adding their energy-absorbing resilience to that of the fetlock. More particularly, as illustrated the lower ends of resilient members 132 are spaced well away from the pivot joints 128 and 130, so that as the lower pivot members are rotated with respect to the upper pivot members, the resilient members 132 are substantially extended, thus reducing the stress on the horse's suspensory ligaments and other vulnerable structures.

As illustrated in FIG. 21, the resilient members 132 may be fabricated of planar rubber or like resilient material. The shape, material and dimensions of the resilient members as well as their attachment positions on the pivot members can be selected to control the rate and actuation angle of the parallel spring. Several parallel slits 132c can be cut into the planar member. The length, width, number and position of the slits can similarly be selected to control the characteristics of the resilient members. The slits can also be used to increase the flexibility of the resilient members and/or to control their shape through the range of motion. By way of example, as shown in FIGS. 17 and 20, during the early stages of extension of the fetlock, the resilient members 132 may be arranged so as take an "S"-shape; when the fetlock is more fully extended, the resilient members 132 straighten out, as shown in FIG. 21, and begin to store energy. The resilient members may also be formed in an "S" shape in their relaxed position. Alternate shapes are possible in both the relaxed position and throughout the range of motion. It is important to control the position and shape of the resilient members throughout the range of motion so as not to create a catch or trip hazard, and to minimize the effect on motion when the spring is not engaged. The ends of the resilient member 132 can be fixed to the upper and lower pivot members on either side, rather than being pivoted freely, to control the disposition of members 132 in the relaxed position; that is, to ensure that the members 132 do take the S-shape shown, rather than, for example, bowing outwardly so as to present a snagging hazard.

Figure 24:
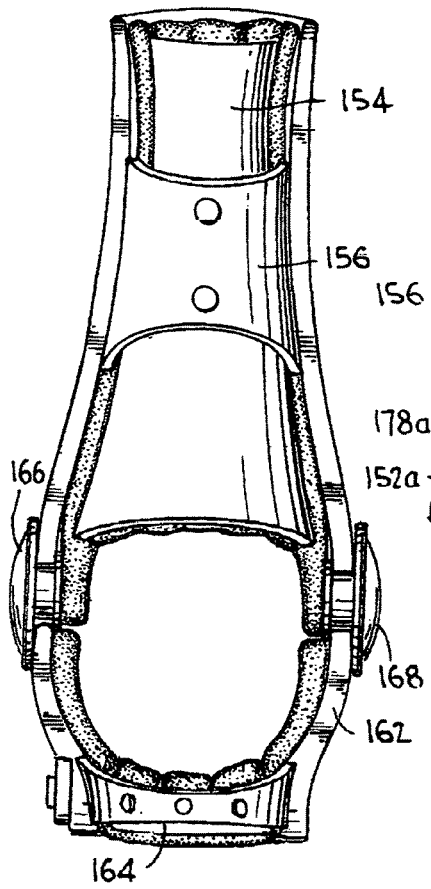
FIG. 24 shows a rear view of the embodiment of FIG. 22.
Figure 25:
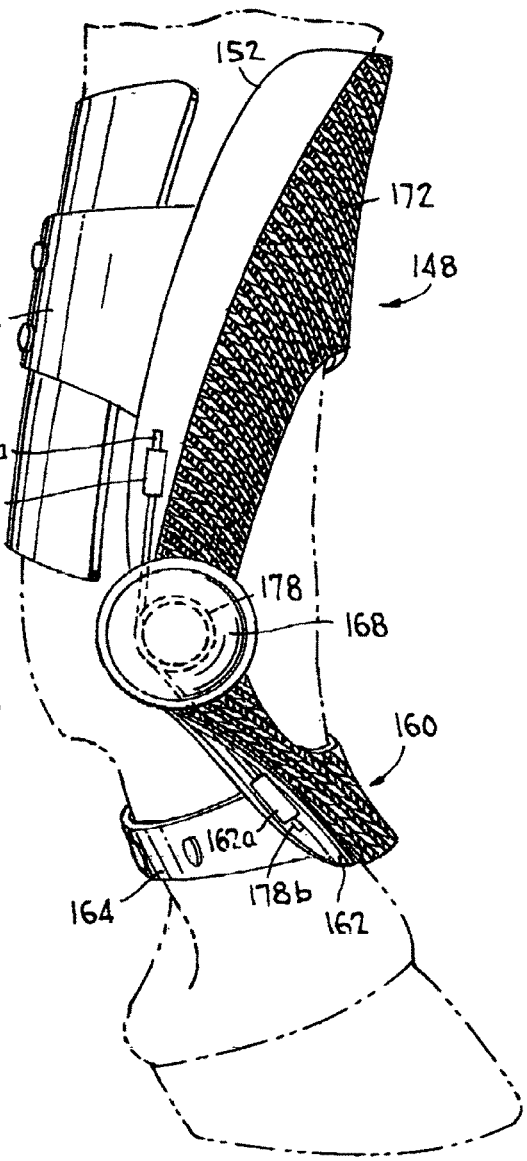
FIG. 25 shows a right-side view of the embodiment of FIG. 22.

FIGS. 22-26 show a third embodiment 150 of the device of the invention, in which FIG. 22 shows a left-side view, with the horse's fetlock shown in phantom, FIG. 23 shows a front view, FIG. 24 a rear view, FIG. 25 a right-side view, and FIG. 26 a top view. In this embodiment, an upper pivoting assembly 148 of the device of the invention 150 comprises a molded forward upper cuff 152 fitting around the forward portion of the horse's leg above the fetlock, and a molded rearward upper cuff 154 fitting around the rearward portion of the horse's leg above the fetlock, and secured to the forward upper cuff 152 by a resilient strap 156 secured to hook 158. In this embodiment, the forward and rearward upper cuffs 152 and 154 are prevented from movement along the limb by being shaped to closely conform to the horse's leg and are secured in place by tension from the stretch of strap 156. The forward and rearward cuffs 152 and 154 are provided with internal padding 170 (see FIG. 26). The device 150 further comprises a lower pivoting assembly 160, comprising a molded saddle member 162 fitting over the forward portion of the horse's leg below the fetlock, and secured there by a strap 164 and hook 165. The upper and lower pivoting assemblies 148 and 160 are pivotably secured to one another at opposed pivot points defined by members 166 and 168. Thus, as the fetlock is extended, as indicated by the arrow B in FIG. 22, the lower pivoting assembly 160 pivots with respect to the upper pivoting assembly 148. In order that the device 150 can support the fetlock, this pivoting is restrained by paired "hairpin" or torsion springs 178 (shown only in FIG. 25) with circular central portions disposed around the pivot points defined by members 166 and 168, with opposed ends 178a, 178b of the springs secured within tunnels 152a, 162a molded into the upper cuff 152 and saddle member 162, to provide spring force absorbing energy in extension of the joint and thus reducing the tendency of the fetlock to be hyper-extended. Other types of spring members, including extension, compression, leaf, etc. might be utilized. Thus, as the fetlock extends, and the lower pivoting assembly 160 pivots with respect to the upper pivoting assembly 148, the spring 178 flexes, adding its spring constant to that of the horse's leg's suspensory structure, and assisting the tendons and related structures in storing energy.

FIGS. 27-30 illustrate an articulated "run-down" protector 180 that can be affixed to the device 150 of FIGS. 22-26 (the run-down protector being illustrated as if secured the device in its FIG. 25, right-side orientation), or to the other embodiments of the protective device of the invention. As illustrated, the run-down protector comprises several "clamshell" interfitting elements 182, molded of hard plastic or the like, all pivoted about members 166 and 168, and arranged so as to open as the fetlock extends (as in FIG. 29), and close, one element 182 sliding towards and possibly underneath the next, as the fetlock returns to its flexed position (as in FIG. 27). Thus, as the horse runs, the protector 180 opens and closes, protecting the rear of the fetlock from contact with the ground or the horse's other hooves. Flexible or resilient material may be provided between the elements 182 to provide additional protection to the rear of the fetlock, reducing abrasion and contact with the ground.

Figure 32:
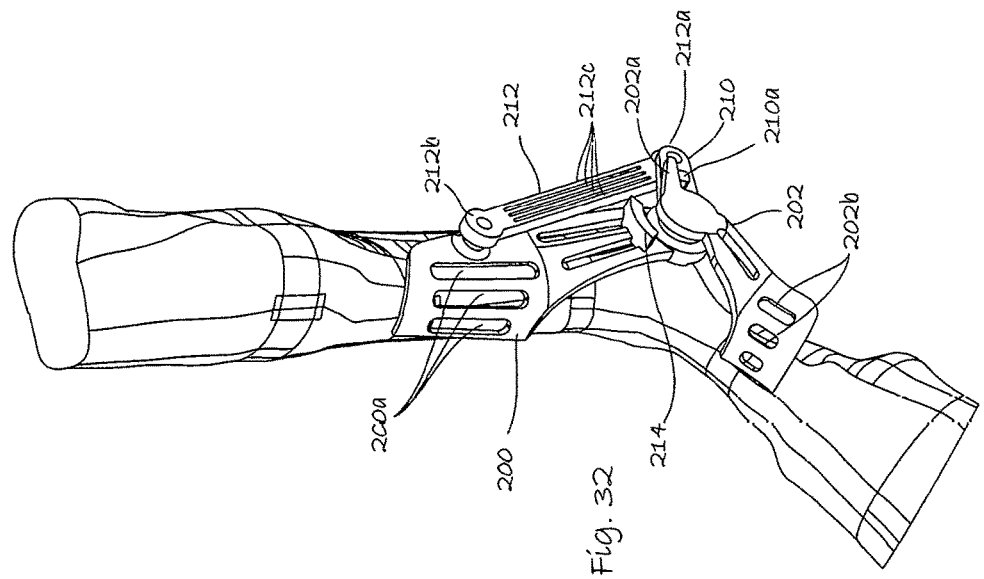
FIG. 32 shows a view similar to FIG. 31, and of the same embodiment, with the joint extended.
Figure 31:
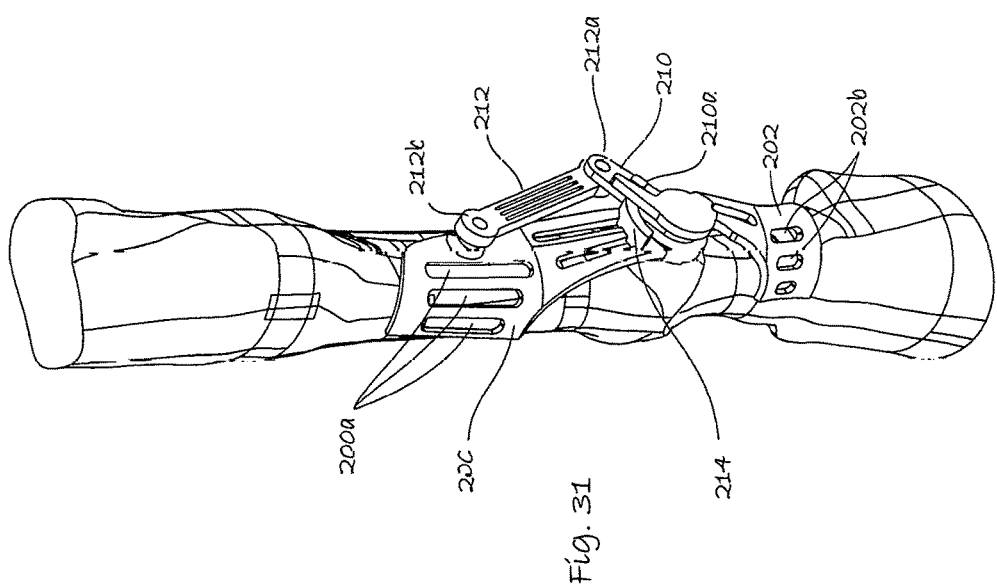
FIG. 31 shows a perspective view of still a further embodiment of the device of the invention, with the joint essentially straight, i.e., neither in extension nor flexion.
Figure 35:
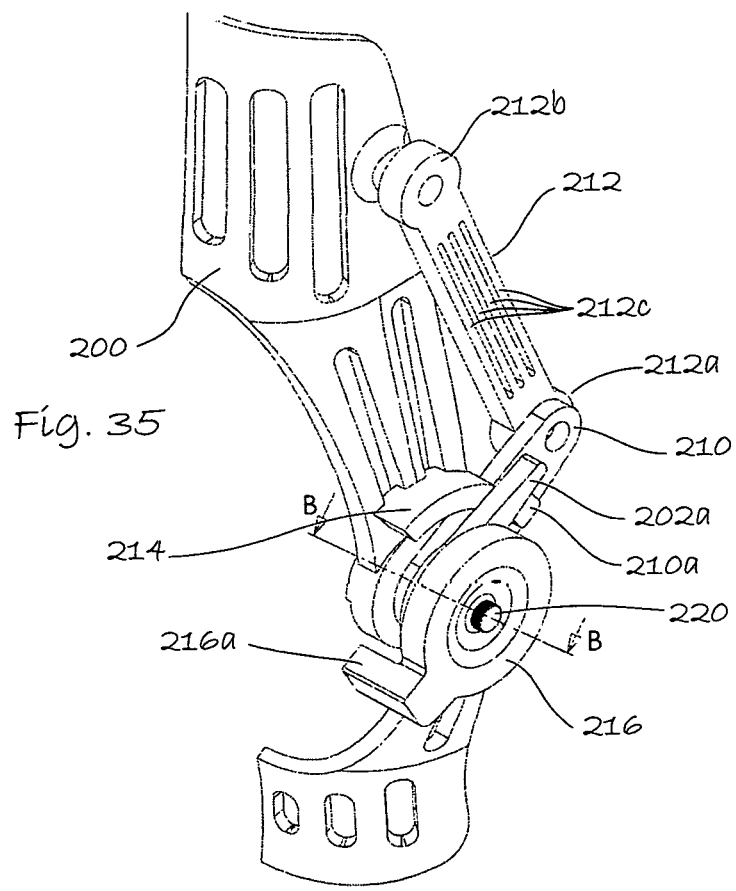
FIG. 35 shows an enlarged view similar to FIG. 33, with the device assembled.
Figure 36:
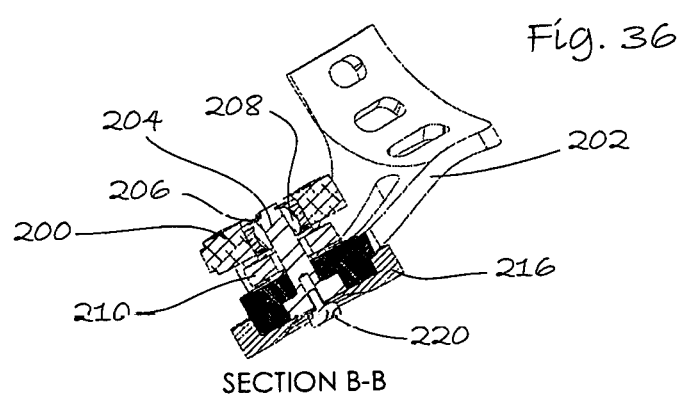
FIG. 36 is a cross-sectional view taken along the line B-B of FIG. 36.
Figure 37:
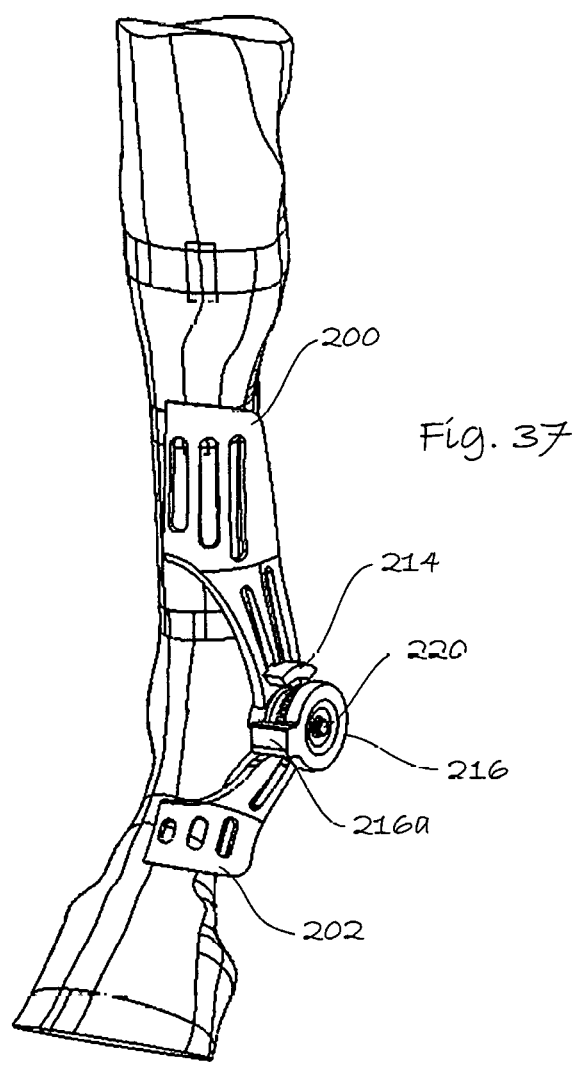
FIG. 37 is a view similar to FIG. 34, illustrating a further modification.
Figure 38:
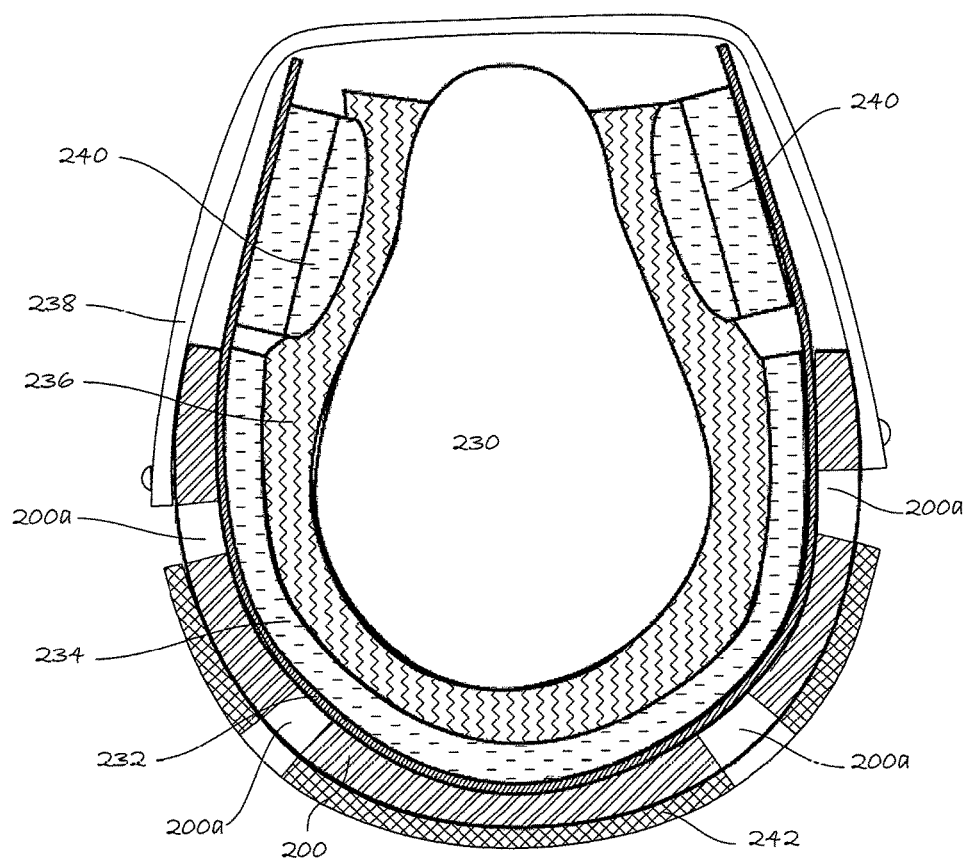
FIG. 38 is a schematic cross-sectional view taken through the device and the joint, illustrating the preferred padding to be employed.

FIGS. 31-40 show several variations on a fourth embodiment of the joint protective device of the invention, wherein a different structure is employed to add support for the tendons of the joint. Again, these embodiments are shown in connection with the fetlock of a horse, but could be adapted to other joints of other animals, including humans. FIGS. 31 and 32 show an embodiment wherein support for the joint only is provided, while FIGS. 33-36, 39 and 40 add structure for limiting the range of motion (ROM) of the joint, particularly useful during rehabilitation after injury or surgery. Finally, FIG. 37 shows an alternative wherein range of motion limitation only is provided. FIG. 38 shows a preferred padding structure. FIGS. 39 and 40 show an alternative construction for the range of motion stop.

Figure 34:
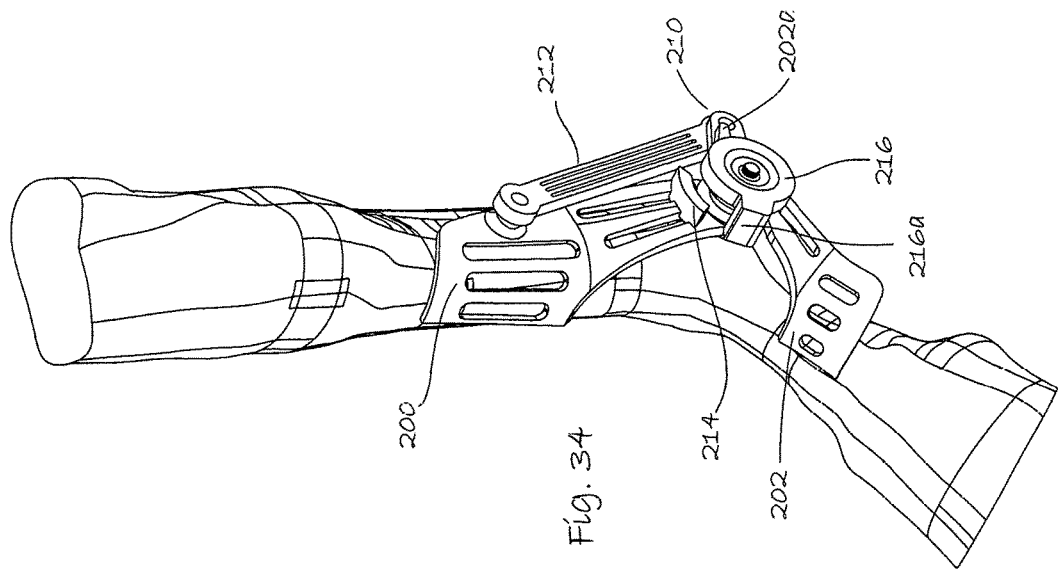
FIG. 34 shows a view similar to FIG. 33, and of the same embodiment, with the joint extended.

In each of FIGS. 31-35, 37, and 39 the device of the invention is shown in part; that is, only one side of the device is shown. Further, FIGS. 31-34 and 37 show the device on the leg of a horse, while FIGS. 35 and 39 show the device half alone. It will be understood that the complete device will include a mirror-imaged opposite side, with upper and lower cuffs of both halves formed integrally. See FIG. 38, discussed below. Thus, in the discussion below, where mention is made of structure on one side of the joint, it will be understood that this refers likewise to like structure on the opposite side of the joint.

Thus, in FIGS. 31 and 32, the device will be seen to comprise an upper cuff 200 and a lower cuff 202. The cuffs, particularly proximal cuff 200, are curved to fit closely over the horse's leg, so that the overall sectional shape of the cuffs is C-shaped in cross-section (see FIG. 38) with the open after portion of the C being wide enough to allow the device to be fitted over a horse's leg. The internal padding detailed in FIG. 38 between the device and the horse's leg compresses to allow the device to thus be fitted over the horse's leg. Straps (shown in FIG. 38) then secure the cuffs over the horse's leg.

Cuffs 200 and 202 are preferably molded of a tough plastic material such as glass-filled nylon or polycarbonate, or possibly aluminum, and may be perforated by vent slots as illustrated at 200a, 202b to save weight and provide some cooling to the joint to be protected. Cuffs 200 and 202 define structure comprising bores through which a pin 204 (see generally FIG. 36, although this is a cross-sectional view taken at B-B of FIG. 35) passes and is retained by, for example, a C-clip 206 on the inside of the upper cuff 200. Thus, cuffs 200 and 202 are joined on either side of the anatomical joint at an axis of rotation located substantially coaxially with the anatomical joint to be protected, in the example, the fetlock of a horse. As illustrated in FIG. 36, pin 204 passes through a bore in a spherical bearing 208 retained in the upper cuff 200. Spherical bearing 208 allows smooth motion of the cuffs with respect to one another in the event of misalignment, and may also allow for some variation in the anatomy of the horse.

An elongated wing member 210 is interposed between the upper and lower cuffs at their joinder and retained by pin 204 received in a bore in one end of the wing member 210. As shown, the opposite end of wing member 210 is secured to the lower end 212a of an elongated resilient tension member 212; the upper end 212b of the resilient tension member 212 is secured to the upper cuff 200, both by joints allowing rotary motion of the ends of the resilient tension member 212 with respect to the wing member 210 and upper cuff 200. Resilient tension member 212 may be fabricated of synthetic elastomeric materials such as ethylene propylene diene monomer (EPDM) or polyurethane, or natural rubber. The tension member 212 can be formed so as to define a number, four in the example shown, of parallel ribbons 212c terminated by circular ends bored to receive fixing pins securing ends 212a and 212b to the wing member 210 and upper cuff 200 respectively. Other designs for the resilient tension member are within the skill of the art.

Wing member 210 pivots freely on pin 204. However, lower cuff 202 is formed to integrally define (or has fixed to it) a rigid finger 202a. Finger 202a rotates together with lower cuff 202 as the joint is extended, i.e., from the position of FIG. 31 to that of FIG. 32, and as it does so finger 202a bears against a block 210a on wing member 210. When this occurs, the wing member 210 is urged clockwise (in the orientation illustrated), exerting tension on resilient tension member 212. Thus, as the joint is extended, tension is exerted on the elongated resilient tension member 212, such that further extension is resisted by a torque exerted on the lower cuff 202 by the wing member 210, and thus absorbing some of the energy that would otherwise have to be absorbed by the tendons of the joint.

One advantage of employing the wing member 210 to thus transmit the motion of the lower cuff 202 to the resilient tension member 212 and thence to the upper cuff 200, as opposed to connecting the resilient tension member directly between the upper and lower cuffs (as in the embodiments of FIGS. 17-21) is that the lower cuff 202 can be permitted to move to a degree before finger 202a bears against block 210a. In the embodiment of FIGS. 17-21 this required that the resilient tension member be S-shaped at rest, so that it did not exert resistance to extension of the joint until it was pulled straight. Thus, design of the resilient tension member 212 is simplified. The packaging of the device is also improved.

Furthermore, the fact that the wing member 210 is freely floating with respect to the lower cuff 202 allows free flexion (counterclockwise from the straight position of FIG. 31) of the joint. More particularly, if the device is worn while a horse is being exercised, as the fetlock goes into flexion (i.e., the hoof goes from extension as in FIG. 32 to straight and continues to rotate so that the hoof comes back and tucks behind the limb, for example when the horse goes over a jump and tucks its hoof up to clear the jump), the wing rotates freely, so that the tension member 212 is not stretched as the lower cuff rotates almost 180 degrees counterclockwise from the extension position of FIG. 32.

Employment of a separate wing also allows more flexibility in the design of the range of motion (ROM) stop, discussed below in connection with FIGS. 33-36, allows disengagement of the resilient tension member 212 by removal of block 210a from wing 210, and allows pretensioning of the resilient tension member 212 without affecting motion in flexion.

Also shown in FIGS. 31 and 32 is a stop 214, which is fixed to the upper cuff 200 and limits the range of motion of wing 210, so as to keep the resilient tension member 212 in the neutral position at any point in the joint's rotation, from full flexion up to the angle where assistive torque begins to be applied by the tensile member, as illustrated in FIG. 31.

It would also be possible to incorporate a further modification that would limit the angular velocity of the joint, beneficial for reasons discussed above. One way to do so would be to employ the d3o dilatant material as a damper on the motion of the lower cuff with respect to the upper cuff, for example by damping the motion of the wing member

210. This could be done by provision of a quantity of the dilatant material in such a way that the dilatant material would be placed in shear upon relative motion of the wing member with respect to the upper cuff. For example, the dilatant material could be disposed within a sealed container having a central member, keyed to pin 204 (FIG. 36) which in this modification would be fixed with respect to upper cuff 200, and an outer shell, rotatable with respect to the central member, and fixed to the wing member 210. Sets of fins on the interior of the container, one set on the central member and one set on the inside of the outer shell, could be arranged so that as the wing member 210 moved with respect to the upper cuff 200, the dilatant material was placed in shear. As the wing member 210 moved faster, the dilatant material would become more resistant to motion, thus limiting the angular velocity of the joint.

Figure 33:
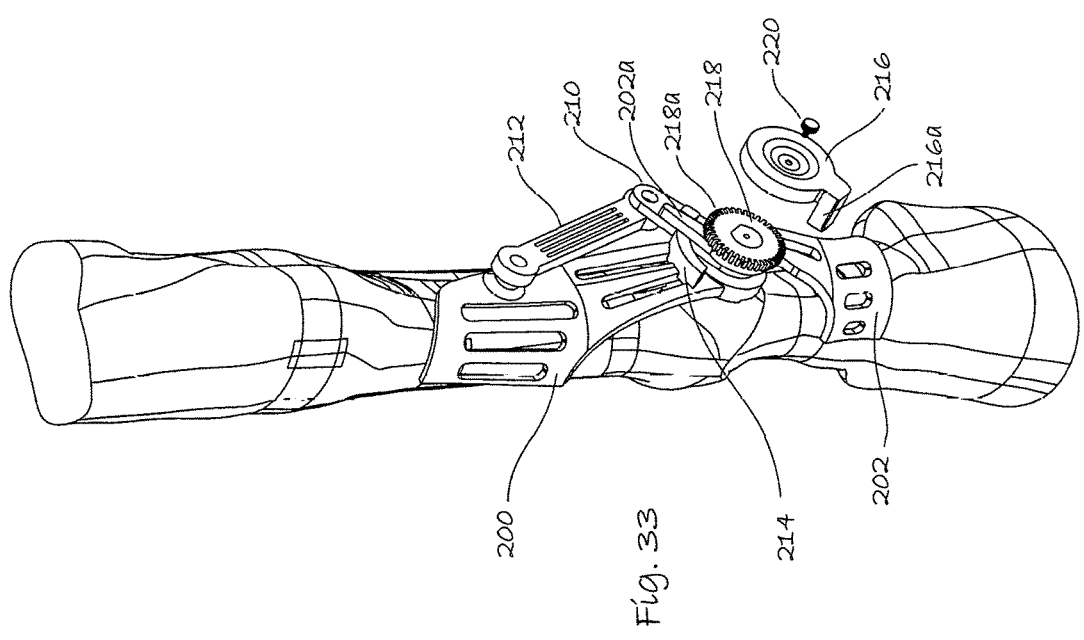
FIG. 33 shows a view similar to FIG. 31, with a further modification shown in partially exploded view, with the joint straight.

FIGS. 33-35 show a further refinement, employing the same structure as explained above with respect to FIGS. 31 and 32, but incorporating as well a range of motion (ROM) stop. Limiting the range of motion of the joint can be helpful in rehabilitation of musculoskeletal structures—again, both hard and soft tissues—after injury or surgery. Early return to function is pivotal to the patient's successful recovery from injury. Some early range of motion exercises help attenuate adhesive scar tissue formation, promote more normal tissue formation, and thereby increase functionality. Muscle atrophy is also less than would occur if the lower limb was completely immobilized. However, unrestricted exercise is counterproductive, setting the stage for reinjury or new lesion formation and a more prolonged and possibly unsuccessful outcome. Adjustment of the ROM to optimize it to the patient's specific recovery status is desirable; generally, as the patient recovers, the ROM can be gradually increased.

This is accomplished in the embodiment shown by providing a ROM stop member 216, held to pin 204 (FIG. 36) by a screw 220. As shown by the exploded view of FIG. 33, a gear wheel 218 having external teeth 218*a* is keyed to the lower cuff 202. The ROM stop member 216 has internal gear teeth (not shown) which mate with the external teeth of gear wheel 218. The mating internal and external peripheral teeth shown could be replaced with radial teeth on the mating faces of the ROM stop member 216 and the lower cuff 202. ROM stop member 216 also comprises an arm 216*a*, which is arranged to bear against stop 214 on the upper cuff 200. Thus, as the joint is extended, ROM stop member 216 rotates along with lower cuff 202 until arm 216*a* contacts stop 214, limiting the ROM of the joint. As the patient recovers, and increased ROM becomes desirable, the relative position of ROM stop member 216 with respect to lower cuff 202 can be adjusted simply by removing screw 220, removing ROM stop member 216 sufficiently to disengage the teeth from one another, turning it counterclockwise and replacing it in its new position.

There are numerous alternative designs for the ROM stop that will occur to those of skill in the art, and are to be considered within the scope of the invention. These include a non-extensible cord, extending between the fixing points of the resilient tension member 212, and of length appropriate to limit the ROM as desired. Adjustment of ROM could be provided by use of cords of different lengths, or providing a choice of fixing points that would provide differing effective lengths. The cord could also be provided in the form of a tubular length of webbing, possibly encasing the resilient tension member 212. Other alternatives include a plate affixed to the upper cuff 200 in the approximate position of stop 214, with a number of holes for receiving a stop pin that would bear against a block on lower cuff 202; by provision of a number of holes for the stop pin, the ROM could be adjusted.

It is also desirable to provide adjustment of the tension exerted by the resilient tension member 212; for example, as the joint recovers from injury or surgery, it may be desirable to gradually reduce the tension exerted for a given degree of joint flexion. This can be accomplished in a variety of ways. For example, one or more of the flat ribbons 212*c* of the resilient tension member 212 can simply be cut away. Different resilient tension members 212 having different characteristics can be employed, or multiple resilient tension members 212 can be employed initially, and be removed progressively as the joint recovers. The attachment point of the resilient tension member 212 on either upper cuff 200 or on wing member 210 can be varied, as can the design of the wing member 210; if the wing member 210 is effectively lengthened, e.g., by proving multiple attachment points along its length, more tension will be exerted for a given degree of joint extension. Likewise, the point at which the resilient tension member 212 begins to exert tension and support the joint can be varied as desired by variation of the geometry of the device.

It will also be appreciated by those of skill in the art that the function of resilient tension member 212 could be provided by other types of devices, such as tension, compression, leaf, hairpin or torsion springs. The cord containing a dilatant material discussed above with respect to FIG. 16 could also be employed. These are to be considered within the meaning of "resilient tension member" except where the context or explicit language excludes such alternative devices.

It is also within the scope of the invention that the device could also be made such that the resilient tension members on either side of the brace could be adjusted independently of one another. For example, it may be desirable to provide more tension on one side than the other when the injury is asymmetric.

As noted, the embodiment of FIGS. 31 and 32 includes the resilient tension member for assistance in bearing the tensile loads on the tendons, while the embodiments of FIGS. 33-35 add to this the ROM stop feature. It is also within the scope of the invention to provide the ROM stop feature without the resilient tension member; this could also be useful in rehabilitation. FIG. 37 shows modification of the device shown to include the ROM stop only. As illustrated, again a ROM stop member 216 is secured to the lower cuff by an arrangement allowing adjustment of their relative radial positions. ROM stop member 216 comprises an arm 216*a* arranged to bear against a stop 214 secured to the upper cuff 200.

As indicated above, FIGS. 39 and 40 show an alternative embodiment of the adjustable ROM stop assembly, wherein the interlocking gears are affixed to the proximal cuff and the fixed stop to the distal cuff. This requires that the relative axial positions of the proximal and distal cuffs at their respective pivot point to be reversed with respect to their positions in the other embodiments, e.g., as shown in FIGS. 35 and 36. Parts performing functions comparable to those discussed in connection with FIGS. 35 and 36 but having different design details are indicated by using the same reference numeral but with a "prime" apostrophe added; thus, the proximal cuff is now denominated 200'. In this embodiment, the wing 210 and resilient member 212 operate as above to support the joint after a desired degree of extension.

Accordingly, in the alternative embodiment of FIGS. 39 and 40, a ROM stop member 216' is provided, secured to pivot pin 204 (FIG. 40) by a screw 220. Pivot pin 204 is secured to the medial side of distal cuff 202' by a circlip 206. A gear wheel 218' having external teeth 218a' is keyed to the proximal cuff 200'. The ROM stop member 216' has internal gear teeth (not shown) which mate with the external teeth 218a' of gear wheel 218'. The mating internal and external peripheral teeth shown could be replaced with radial teeth on the mating faces of the ROM stop member 216' and the proximal cuff 200'. ROM stop member 216' also comprises an arm 216a', which is arranged to bear against a stop 214' on the distal cuff 202'. Thus, as the joint is extended, distal cuff 202' moving clockwise in FIG. 39, stop 214' rotates along with distal cuff 202' until stop 214' contacts arm 216a', limiting the ROM of the joint. As the patient recovers, and increased ROM becomes desirable, the relative position of ROM stop member 216' with respect to proximal cuff 200' can be adjusted simply by removing screw 220, removing ROM stop member 216' sufficiently to disengage the teeth from one another, turning it clockwise and replacing it in its new position. A thrust bearing 211 is interposed between proximal cuff 200' and distal cuff 202' to prevent galling. Wing 210, finger 202a and resilient member 212 may be provided and function as described above.

FIG. 38 shows a cross-sectional view of the padding structure preferably employed between the device as discussed previously and the leg 230 of a horse. In the example, this is taken though the upper cuff 200, showing the vent slots 200a. As shown, the upper cuff 200 is generally C-shaped in section, and is made of a material, possibly plastic or aluminum as discussed above, the principal considerations being that it be strong enough to withstand the significant load to be applied without deformation, light in weight, relatively easily manufactured, and not excessive in cost. The cuff is then secured over the leg 230 by straps indicated schematically at 238. Outside the cuff there may be provided a layer 242 of an impact-absorbing material, such as the d3o dilatant material discussed above.

Immediately inside the cuff 200 is a backer layer 232. The function of this is to distribute the strap load at the conformal layer 240 (discussed further below) and provide attachment of the inner layers to the cuff 200. The backer layer 232 can be a thin plastic sheet, or could be molded of plastic, e.g. polypropylene or polyethylene. The backer layer 232 need not follow the entire C-shape, as illustrated.

Inside the backer layer 232, roughly coextensive with the cuff 200, as shown, is a cushion layer 234. Its purpose is to transfer and distribute loads, that is, so as to avoid point loading on the joint, which would be painful. The cushion layer 234 can be made of open or closed cell foam, a spacer fabric, a thin gel, disposed in a conformable container, or the like. These materials are chosen in part to allow some motion under shear, that is, so that the device can move somewhat as the joint is extended and flexed without relative motion or focal loading between the device and the horse's skin, thus avoiding pressure necrosis and focal abrasion.

Toward the open ends of the backer layer are disposed two members 240, referred to collectively as the conformal layer. The function of these members is again to distribute loads near the tendon area at the rear of the joint, and provide a good anatomical fit. The material of these members can be open or closed cell foam, thermoplastic urethane, a gel (again provided in a conformable container), an air bladder, or other like materials or combinations of materials. These materials are also chosen, as in the case of the cushion layer 234, to allow some movement under shear forces.

Finally, the innermost leg surface layer 236 is provided to provide a low-abrasion surface against the horse's leg. This layer can be made of woven materials, such as plush fleece material, or natural materials such as sheepskin or reindeer fur, or the like.

While the device of the invention has been disclosed in terms of preventing injury to the musculoskeletal structures of the equine fetlock, and for use in rehabilitation after injury or surgery, the principles of the invention can similarly be used by those of skill in the art to prevent injury to or assist in rehabilitation of other joints, as well as those of other animals and of humans. It should also be recognized that while the invention has been disclosed in embodiments that variously limit the range of motion of the joint, limit its maximum angular velocity, and provide a tensile member to help reduce the loading on the tendons of the limb during extension, there may be cases wherein only one or two of these functions is desired.

Accordingly, while several preferred embodiments of the invention have been disclosed in detail, the invention is not to be limited thereto but only by the following claims.

What is claimed is:

1. A joint support device for limiting a range of motion of a joint disposed between a proximal and distal section of a limb, said joint defining an axis of rotation, comprising:
   a proximal cuff, adapted to fit closely about said proximal section of said limb, and be secured thereto;
   a distal cuff, adapted to fit closely about said distal section of said limb, and be secured thereto;
   said proximal and distal cuffs each comprising medial and lateral structure comprising bores for receiving medial and lateral pivot pins, such that said proximal and distal cuffs can be assembled to one another for relative pivoting, thus defining an axis of rotation adapted to be substantially aligned with the axis of rotation of said joint; and
   a first toothed gear secured to one of said proximal and distal cuffs and a second toothed gear adapted to be secured to said first toothed gear with the teeth of said gears engaged so as to prevent relative motion thereof, said second toothed gear having a first stop fixed thereto and adapted to contact a second stop adapted to be secured to the other of said proximal and distal cuffs to limit the range of motion of said joint, wherein said second toothed gear can be disengaged from said first toothed gear, their relative positions adjusted, and be resecured to and reengaged with said first toothed gear, whereby the position of said first stop relative to said second stop can be selected to controllably limit the range of motion of the joint.

2. The device of claim 1, further comprising structure for limiting an angular velocity of the joint while allowing pivoting thereof.

3. The device of claim 1, wherein said first toothed gear is generally circular and has external teeth on a peripheral edge thereof, and said second toothed gear is generally circular and has internal teeth, whereby said second toothed gear is moved axially with respect to said first toothed gear to allow adjustment of their relative positions.

4. The device of claim 1, wherein said first toothed gear is secured to the proximal cuff and said second stop is secured to the distal cuff.

5. The device of claim 1, further comprising one or more elongated resilient members connected between the proximal and distal cuffs so as to be placed under tension during extension of the joint, supporting the joint.

* * * * *